(12) United States Patent
Tennican

(10) Patent No.: US 10,864,361 B2
(45) Date of Patent: Dec. 15, 2020

(54) FRICTION FIT MEDICAL CAPS

(71) Applicant: Hyprotek, Inc., Spokane, WA (US)

(72) Inventor: Patrick O. Tennican, Spokane, WA (US)

(73) Assignee: Hyprotek, Inc., Spokane, WA (US)

( * ) Notice: Subject to any disclaimer, the term of this patent is extended or adjusted under 35 U.S.C. 154(b) by 233 days.

(21) Appl. No.: 15/753,296

(22) PCT Filed: Aug. 18, 2016

(86) PCT No.: PCT/US2016/047581
§ 371 (c)(1),
(2) Date: Feb. 17, 2018

(87) PCT Pub. No.: WO2017/031332
PCT Pub. Date: Feb. 23, 2017

(65) Prior Publication Data
US 2018/0243545 A1    Aug. 30, 2018

Related U.S. Application Data

(60) Provisional application No. 62/207,311, filed on Aug. 19, 2015.

(51) Int. Cl.
*A61M 5/00*     (2006.01)
*A61M 39/02*    (2006.01)
(Continued)

(52) U.S. Cl.
CPC ........ *A61M 39/0247* (2013.01); *A61M 5/001* (2013.01); *A61M 39/162* (2013.01); *A61M 39/20* (2013.01); *A61B 5/15003* (2013.01); *A61M 2005/3104* (2013.01); *A61M 2039/0258* (2013.01); *A61M 2039/0285* (2013.01);
(Continued)

(58) Field of Classification Search
CPC . A61M 5/001; A61M 39/0247; A61M 39/162
See application file for complete search history.

(56) References Cited

U.S. PATENT DOCUMENTS

| | | | |
|---|---|---|---|
| 6,632,199 B1 | 10/2003 | Tucker et al. | |
| 2010/0064456 A1 * | 3/2010 | Ferlic | A61L 2/235 15/104.94 |
| 2015/0086441 A1 | 3/2015 | She et al. | |

FOREIGN PATENT DOCUMENTS

| | | |
|---|---|---|
| CA | 480166 | 1/1952 |
| WO | WO2015032715 | 3/2015 |

OTHER PUBLICATIONS

The PCT Search Report and Written Opinion dated Oct. 26, 2016 for PCT application No. PCT/US2015/047581, 11 pages.

\* cited by examiner

*Primary Examiner* — Kevin Joyner
(74) *Attorney, Agent, or Firm* — Lee & Hayes, P.C.

(57) ABSTRACT

A port cap has a closed end, an open end, and a conical body made of a flexible material. An inside of the port cap may have a textured or uneven surface. The textured or uneven surface may be formed by one or more annular rings. An annular ring may be asymmetrical having different slopes on the two different sides of the annular ring. The port cap may be made of an elastomeric polymer or elastomeric copolymer. An insert inside the port cap may be made of a sponge or similar material and may contain a cleaning agent or microbiocidal. The port cap may be sealed with a lid. Methods of using the port cap are also disclosed.

15 Claims, 21 Drawing Sheets

(51) Int. Cl.
     *A61M 39/16*        (2006.01)
     *A61M 39/20*        (2006.01)
     A61M 5/31          (2006.01)
     A61B 5/15          (2006.01)

(52) U.S. Cl.
     CPC ............... *A61M 2039/0288* (2013.01); *A61M 2205/0205* (2013.01); *A61M 2205/0216* (2013.01); *A61M 2205/0238* (2013.01); *A61M 2205/584* (2013.01); *A61M 2209/06* (2013.01)

FRICTION FIT MEDICAL CAPS

CROSS REFERENCE TO RELATED APPLICATIONS

This application is the National Stage of International Application No. PCT/US16/47581, filed Aug. 18, 2016, which claims the benefit of U.S. Provisional Patent Application No. 62/207,311, filed on Aug. 19, 2015, and entitled "FRICTION FIT MEDICAL CAPS." The entire contents of the above-referenced applications are incorporated herein by reference.

TECHNICAL FIELD

The invention pertains to intravascular port access devices, intravascular port cleaning devices, methods of cleaning an intravascular port, methods of administering an agent into an intravascular line port, methods of obtaining a blood sample from an individual, and intravascular line port caps.

BACKGROUND OF THE INVENTION

Intravenous lines, such as peripheral IV lines and central IV lines, are common intravenous access methods for administering medicants, nutrient solutions, blood products, or other substances into a vein. Arterial lines are used, for example, in monitoring physiological parameters by arterial blood sampling during coronary, intensive or critical care. However, microorganism intravascular device colonization or infection can occur as a result from a patient's own endogenous flora or from microorganisms introduced from contaminated equipment or other environmental contamination sources. As a result, localized or systemic infection or septicemia can occur and can be life threatening.

Introduction of microorganisms into an intravenous line can be initiated or facilitated during handling of a catheter, hub, associated tubing, equipment, or injection ports, especially during manipulation of lines in preparation and during initiation of fluid administration into or withdrawal from the line. Microorganisms present on a surface of an injection port can be introduced through the port during administration. Microorganisms present on contaminated equipment utilized for administration can be introduced through the port causing colonization or infection. Bacterial growth and/or aggregation in a port or catheter can serve as the nidus for clotting, embolization and/or occlusion of the port or catheter. Further manipulation or administration through the port can facilitate spreading of microorganisms within the port, catheter, and lines, and ultimately into the patient's vein/artery and/or surrounding tissue. Accordingly, it would be advantageous to develop methods and devices for cleaning of external surfaces of intravascular access ports and/or internal port areas to reduce risks of colonization and infection.

Another complication that can occur in association with an intravascular line, catheter or access port is clot formation due to blood return. Initial clot formation could extend and/or embolize into the superior vena cava and/or the right atrium and/or right ventricle of the heart, and subsequently into the pulmonary system circulating to the lungs. It would be advantageous to develop methodology and devices to deliver clot dissolving or clot inhibitory agents through intravascular ports to minimize or eliminate intravascular port associated clotting.

Yet another issue that can be associated with intravascular lines is lipid accumulation or build-up within the line or port. It would be advantageous to develop methodology and devices to deliver lipolytic agents through intravascular ports to minimize or eliminate port associated lipid build up.

SUMMARY OF THE INVENTION

In one aspect the invention pertains to an intravascular port access device. The device includes a first component having a chamber and being configured to attach reversibly to an intravenous line port. The second component reversibly attaches to the first component and contains a disinfecting agent and an applicator material such as polyethylene felt sponge, polyethylene foam sponge, plastic foam sponge, silicon foam sponge, and the like. The second component is configured to be reversibly received over external surfaces of the intravenous line port.

In one aspect, the invention encompasses an intravascular line port cleaner including a syringe barrel having a first end and a second end. A slideable piston is received into the barrel through the second end. The line port cleaner includes a first cap containing a cleansing agent and a second cap containing a microbiocidal agent.

In one aspect, the invention encompasses a method of cleansing an intravenous line port. The method includes providing a port cleaning device comprising a first component having a chamber with a first cleaning agent. A second component includes a second cleaning agent. A third component has a microbiocidal agent and is reversibly attached to the first component. The method includes removing a second component from the device, contacting the external surfaces of the port with the second cleaning agent, injecting the first cleaning agent from the chamber into the port, removing the third component from the device, and capping the port with the third component.

In one aspect the invention encompasses a method of obtaining a blood sample from an individual. The method includes providing a port access device having a first component including a chamber, a second component containing a cleaning agent and a third component comprising a microbiocidal agent. The third component is reversibly attached to the first component. The method includes removing the second component from the device and contacting the external surfaces of the port with the cleaning agent. The method further includes drawing blood from the individual through the port into the chamber of the first component removing the third component from the device and capping the port with the third component.

In one aspect the invention includes a set of intravascular line port caps. The set of caps includes a first port cap containing a first agent and a first applicator material. The set further includes a second port cap containing a second agent and a second applicator material.

BRIEF DESCRIPTION OF THE DRAWINGS

Aspects of the invention are described below with reference to the following accompanying drawings.

DETAILED DESCRIPTION

In general, the invention includes devices and methodology for cleaning and/or accessing intravascular line ports. In particular applications devices of the invention can be used for cleaning external surfaces of an intravascular line port followed by cleaning of the port itself and in particular instances cleaning of intravascular lines.

In other applications devices of the invention can be utilized for administering an agent intravascularly. During these applications, the devices in accordance with the invention can typically be utilized to cleanse external surfaces of the port prior to utilizing the device for administering of an agent intravascularly. In another application devices of the invention can be utilized to obtain a blood sample from an individual. A device in accordance with the invention is typically utilized to cleanse external surfaces of a port prior to utilizing the device to withdraw a sample of blood from the port. The invention also includes methodology for such port cleansing agent administration and blood sampling techniques.

In one embodiment, the device comprises two components. An example two component device is described with reference to FIGS. 1-5.

Figure 1:
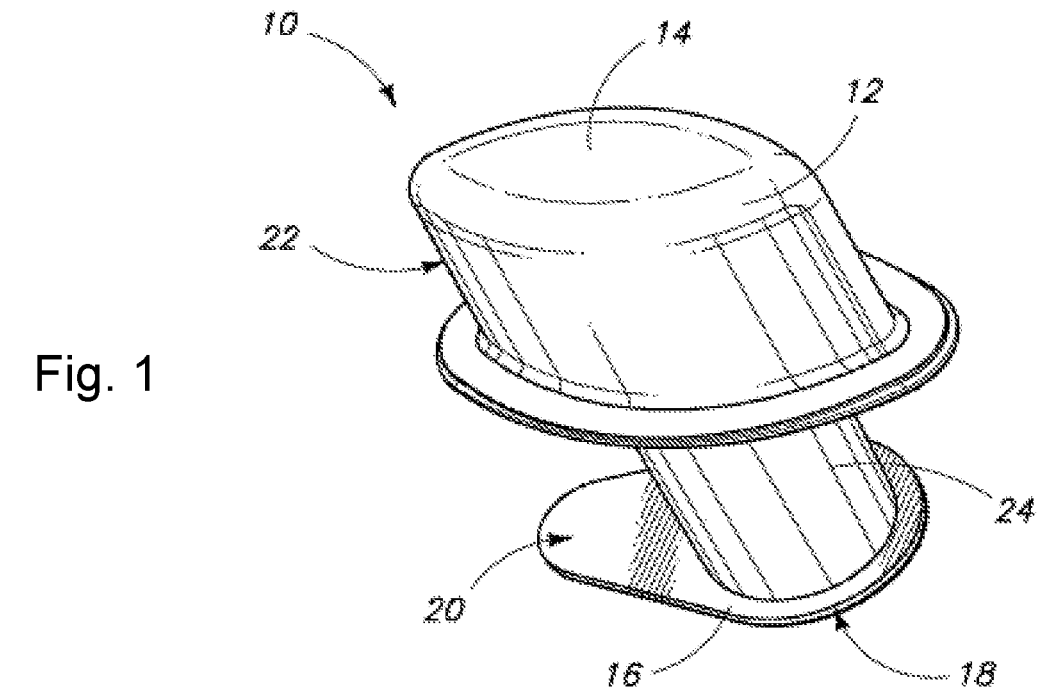
FIG. 1 is a diagrammatic isometric view of a device in accordance with one aspect of the invention.
Figure 2:
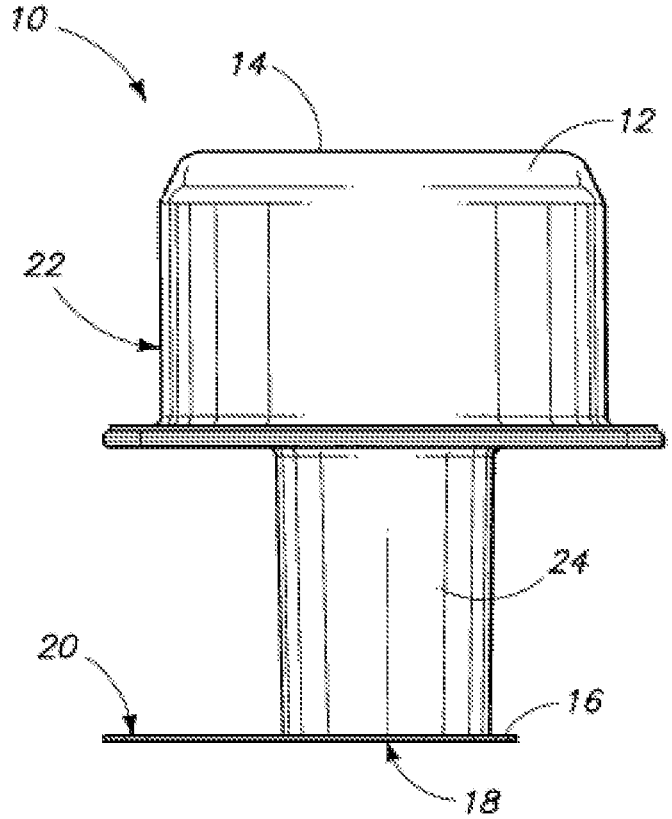
FIG. 2 is a diagrammatic side view of the device shown in FIG. 1.

Referring initially to FIG. 1, a port access device 10 comprises a first component 12 at a first end 14 of the device, and a second component 16 at a second end 18 of the device. Second component 16 can have a tab 20 or other extension feature for assisting removal of the second component from the first component. First component 12 has a chamber housing 22 which can be a collapsible housing. First component 12 can also comprise an extension portion 24. Referring to FIG. 2, as depicted device 10 can have second portion 16 insertable within connector portion 24. It is to be understood however that the invention contemplates other configurations wherein second portion 16 fits over or caps extension portion 24. It is also to be understood that the shape and dimension of collapsible housing 22 is but an example with alternative shapes, sizes and configurations contemplated.

Figure 3:
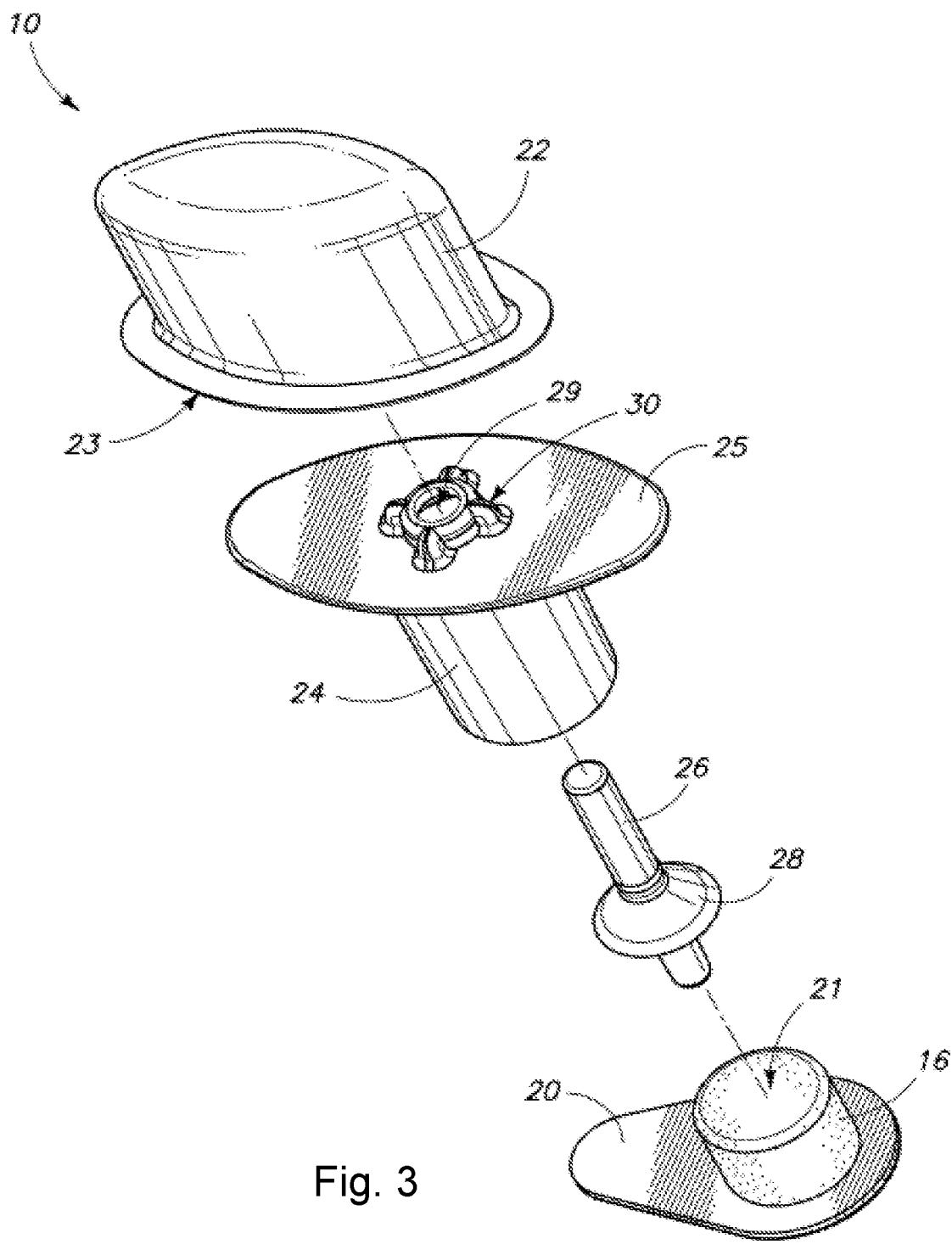
FIG. 3 is a diagrammatic exploded view of the device shown in FIG. 1.

Referring to FIG. 3 such shows an exploded view of the device depicted in FIGS. 1 and 2. As illustrated chamber housing 22 of device 10 can house a chamber 23. Connector 24 can comprise a separator 25 having an opening 29 passing therethrough. Connector 24 can further comprise a receiving port 30 for receiving a dispenser 26. Dispenser 26 in turn can comprise a valve portion 28. Second component 16 can comprise a container 21.

Figure 4:
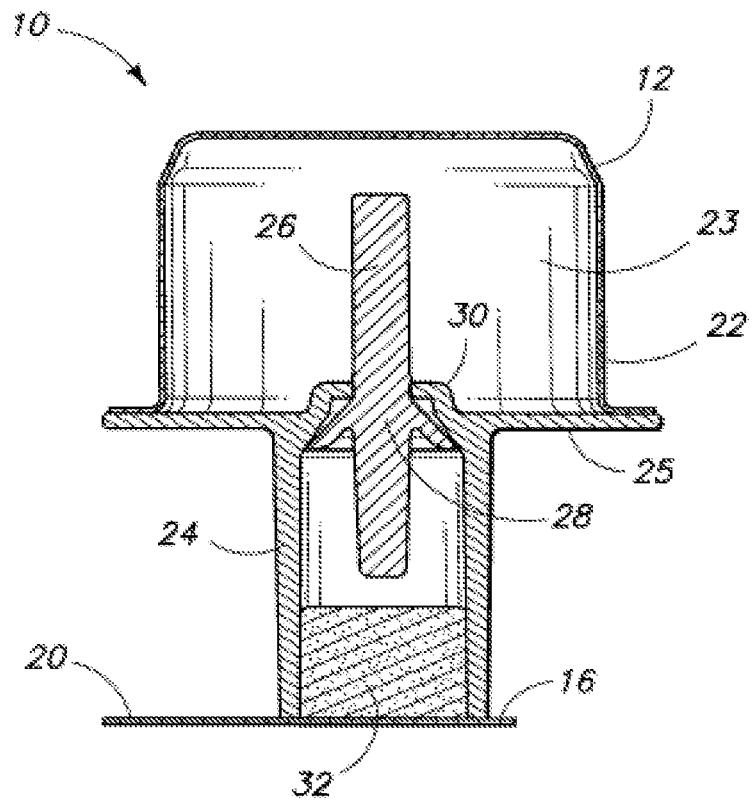
FIG. 4 is a diagrammatic cross-sectional view of the device shown in FIG. 1.
Figure 5:
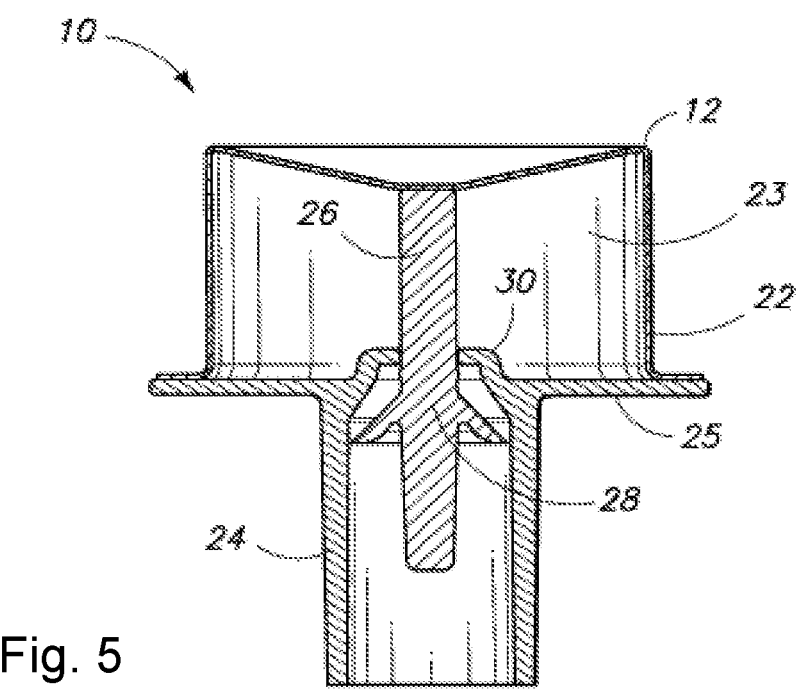
FIG. 5 is a diagrammatic cross-sectional view of the device shown in FIG. 1 after repositioning relative to the positioning depicted in FIG. 4.

Referring next to FIG. 4, such shows dispenser 26 with valve 28 seated within receiving port 30. As depicted such valve mechanism is in the "closed" position where contents of chamber 23 are blocked from passing into or through connector 24. Referring next to FIG. 5, application of force upon collapsible housing 22 such as a downward pressure upon a top surface of the housing can be utilized to displace valve device 28 from receiving port 30 as illustrated. Such displacement can allow passage of the contents of chamber 23 into or through connector portion 24.

As depicted in FIG. 4, second component 16 can contain an applicator material 32. Such applicator material can be for example, a sponge or sponge-type material. Exemplary sponge-type materials can include but are not limited to polyethylene felt sponge, polyethylene foam sponge, plastic foam sponge, and silicon foam sponge.

Where device 10 is to be utilized for port cleansing applications, container 21 of second component 16 will typically contain a cleansing agent. The cleansing agent can be a disinfecting agent for cleansing external port surfaces. The agent is not limited to a particular cleaning or disinfecting agent and can comprise for example alcohol, such as an alcohol solution comprising from about 5% to about 99% alcohol. In particular applications the alcohol solution will comprise 25% to 90% alcohol. The sponge-type applicator material can be utilized to assist in containing the cleansing agent and can further assist in applying the agent to external surfaces of the intravascular port. Second component 16 is removably attached to the device 10. For cleansing of the port, removable component 16 is removed from first component 12 and is utilized to contact external port surfaces for cleansing of external portions of an intravascular line port.

After cleansing of external portions of the port, the first component of the device, which in cleansing/disinfecting applications can be utilized for internal cleansing of the intravascular port, can be reversibly attached to the port to be cleansed. The chamber volume can be for example up to 3.5 ml; a preferred volume range can be from about 1 to about 3 ml although alternative chamber sizes for smaller or larger volumes are contemplated. The chamber can have appropriate calibration marks relative to the total volume of the chamber. For example, a 3.5 ml. fluid volume chamber can have volume markings every 1 ml, every 0.5 ml, every 0.1 ml, etc. In particular embodiments, the connector portion can have a LEUR-LOK® (Becton, Dickinson and Company Corp., Franklin Lakes N.J.) fitting (not shown) for connection to a LEUR-LOK® type port. A cleansing agent can be provided within chamber 23 and can be an antibiotic or an alternative appropriate disinfectant. An exemplary agent can be an alcohol or alcohol solution such as described above relative to the second component container 21. In cleansing applications chamber 22 can alternatively or additionally contain chemical agents including ethylene diamine tretaacetic acid (EDTA) and/or sodium citrate.

Once connected to the line port external pressure can be applied to collapsible housing 22 by for example squeezing, pinching, or pushing inward on the housing to displace dispenser 26 thereby opening or displacing valve 28 from receiving port 30. Continued squeezing or external force can be utilized to dispel or eject contents of chamber 23 through connector 24 and into the connected port. Depending upon the volume of chamber 23 the injected cleansing solution may extend into the intravascular line itself. After dispelling the contents of chamber 23 device component 12 can be removed from the port to allow administration of fluids to be delivered intravascularly (for example). If such delivery is not to be performed immediately upon cleansing, component 12 of the cleansing device can be retained on the port until such time as intravascular delivery is desired.

In another aspect, the above-described device and methodology can be utilized for administering an anti-clot agent to minimize or prevent intravascular associated clot formation or to dissolve an existing clot. In this aspect, rather than or in addition to the antimicrobial agent, chamber 23 can contain an appropriate anticoagulant agent or clot dissolving agent. Exemplary anti-clot agents which can be utilized include but are not limited to anticoagulants such as EDTA, sodium citrate, heparin and heparin derivatives, and anti-thrombolytic agents such as tissue plasminogen activator. Where lipid accumulation is an issue an appropriate dispersion or lipolytic agent can be administered, either independently or in combination with antimicrobial agent and/or anti-clot agent. Injection of any such agents can be achieved in a manner analogous to that described above relative to the cleansing agent. These applications may also be accomplished utilizing the embodiments illustrated and described below.

Figure 6:
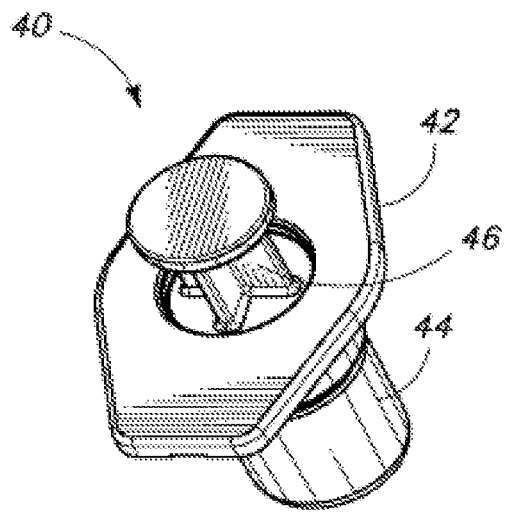
FIG. 6 is a diagrammatic isometric view of a device in accordance with another aspect of the invention.
Figure 7:
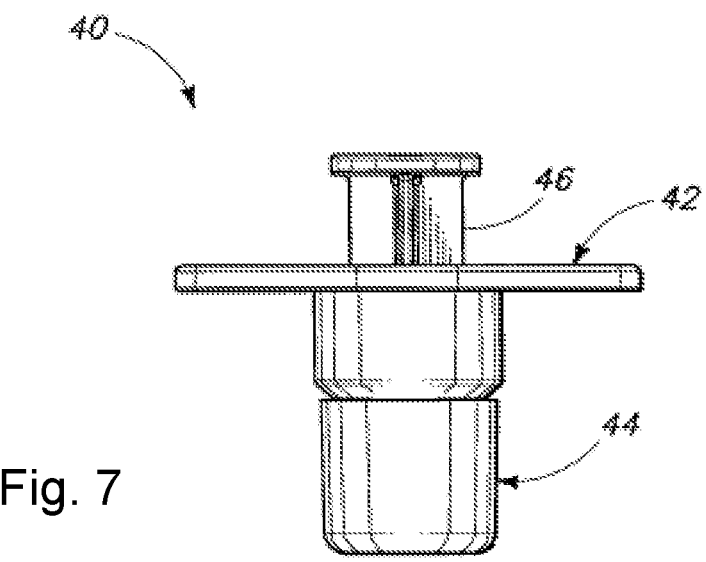
FIG. 7 is a diagrammatic side view of the device shown in FIG. 6.
Figure 8:
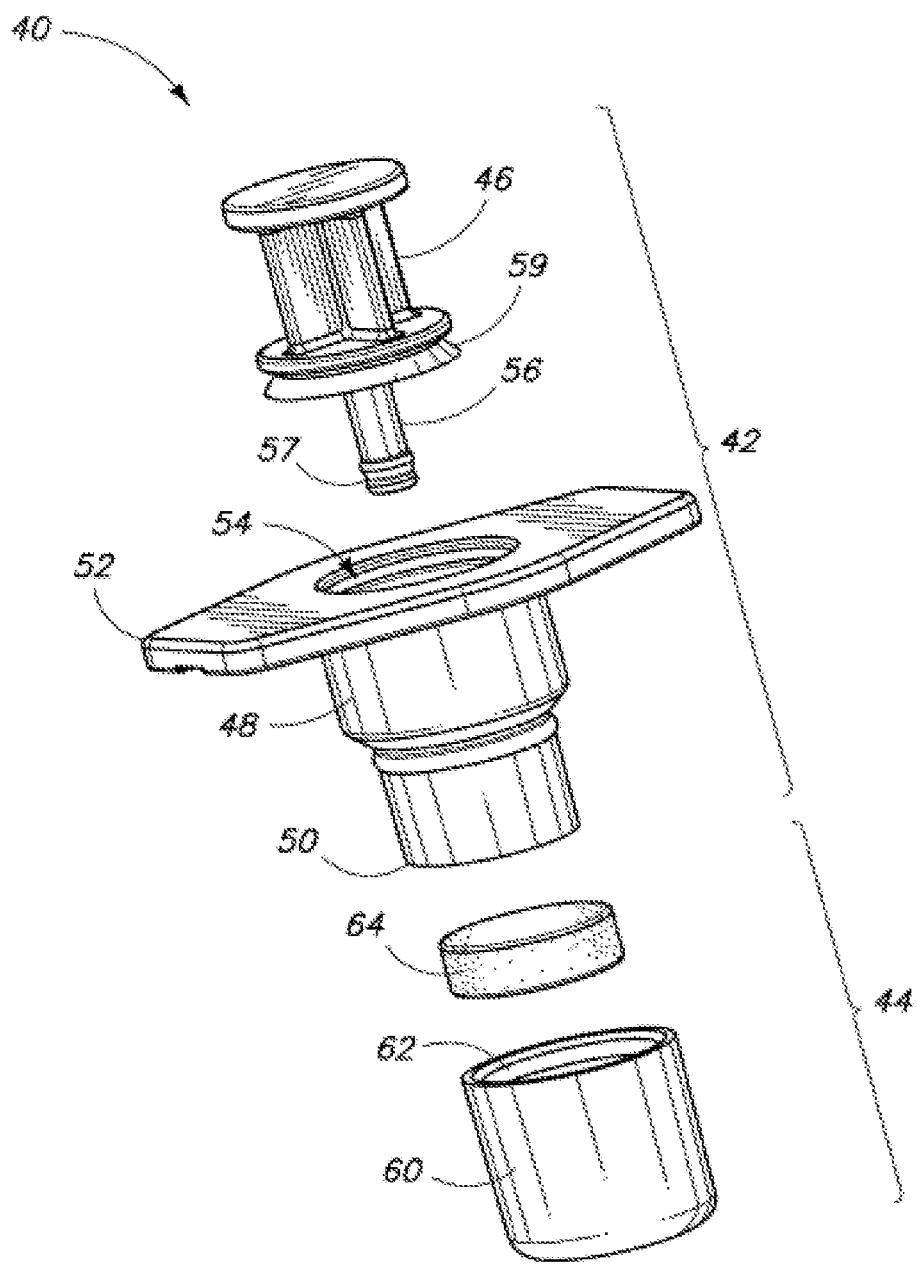
FIG. 8 is a diagrammatic exploded view of the device of FIG. 6.

An alternative embodiment of a device in accordance with the invention is illustrated and described with reference to FIGS. 6-11. Referring to FIG. 6, such illustrates an alternative example port access device 40 having a syringe-like first component 42 and a second component 44. Referring to FIG. 7 syringe-like first component 42 includes a plunger 46. An exploded view of the port access device is depicted in FIG. 8. First component 42 includes a syringe barrel-like housing 48 having a first end 50 and a second end 52 with an internal chamber 54. Chamber 54 may have a fluid volume of from 1 to about 3.5 ml. Housing 48 can have appropriate calibration marks as discussed above with respect to the earlier embodiment.

Plunger 46 can include a stem portion 56 having a seal 57. Plunger 46 can be insertable into second end 52 of housing 48. A second seal 59 can be associated with the larger diameter body of the plunger. Seal 59 is present to form a seal between the plunger and an internal surface of the device chamber. Seal 59 can be an elastameric seal which is overmolded onto the piston (which can be a molded hard plastic material). However, the invention contemplates alternative seal material and use of non-overmolded techniques.

Seal 57 can be a single seal or a set of seals and can be for example a set of two a-rings, a single broad overmolded elastameric O-ring or sleeve or a hard plastic seal molded integrally with the piston stem. The presence of seal 57 can advantageously inhibit or prevent unwanted or unintentional backflow of fluid into the device chamber thereby decreasing the risk of contamination of the device and/or its contents. Alternatively, relative to the depicted configuration a single seal can be over molded to have a base portion which forms the seal between an internal wall of the device chamber and the large diameter portion of the piston and a sleeve portion which covers the walls of the smaller diameter portion of the piston (not shown).

The second component 44 is a removable cap portion having a housing 60 and an internal container 62. Container 62 can contain an applicator material 64. The applicator material can be, for example, any of those materials discussed above with respect to the earlier embodiment. The second component 44 can additionally contain a cleansing agent such as those cleansing agents discussed above. Second component 44 can be configured to fit over or onto an intravascular port such that the cleansing agent can be applied to external surfaces of the port. Such cleaning can be conducted prior to administering the contents of chamber 54 (for example, an anticlot, antimicrobial or other cleansing agent) into the port. However, post-administration cleansing of the port utilizing the removable cap portion is also possible.

Figure 9:
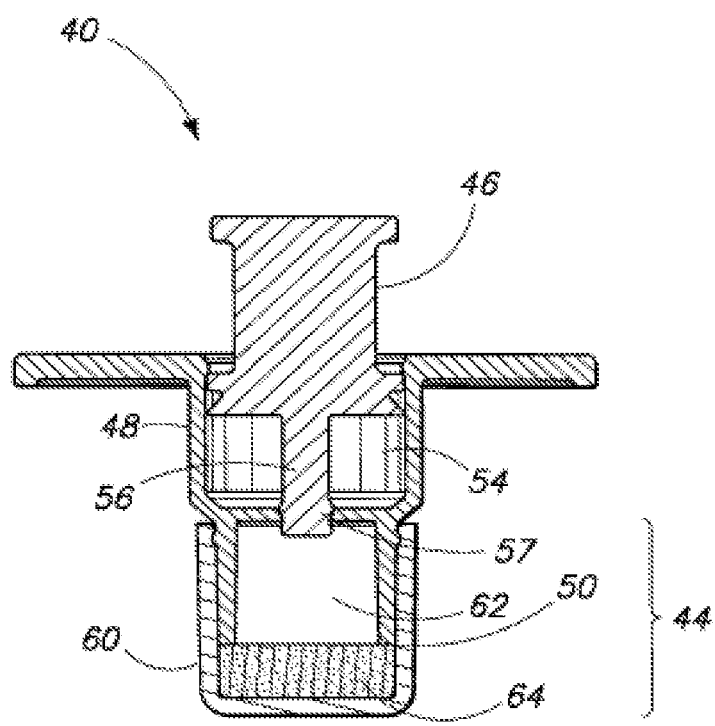
FIG. 9 is a diagrammatic cross-sectional view of the device shown in FIG. 6.

Referring next to FIG. 9, such shows a cross-sectional view of the embodied device 40 in an intact configuration. For utilization second component 44 can be removed and utilized to cleanse external surface of the port. Subsequently, first end 50 of the second component can be attached to the port and contents of the chamber 54 can be administered into the port by application of force to plunger 46. Alternatively, chamber 54 can be provided empty or can be provided to contain, for example, an anticoagulant agent and device 40 can be provided with plunger 46 in a forward position. Thus device 40 can be utilized for applications such as obtaining and/or testing of a blood sample from an individual by attaching first end 50 of the device to the port and repositioning of plunger 46 to draw fluid through the port into chamber 54.

Figure 10:
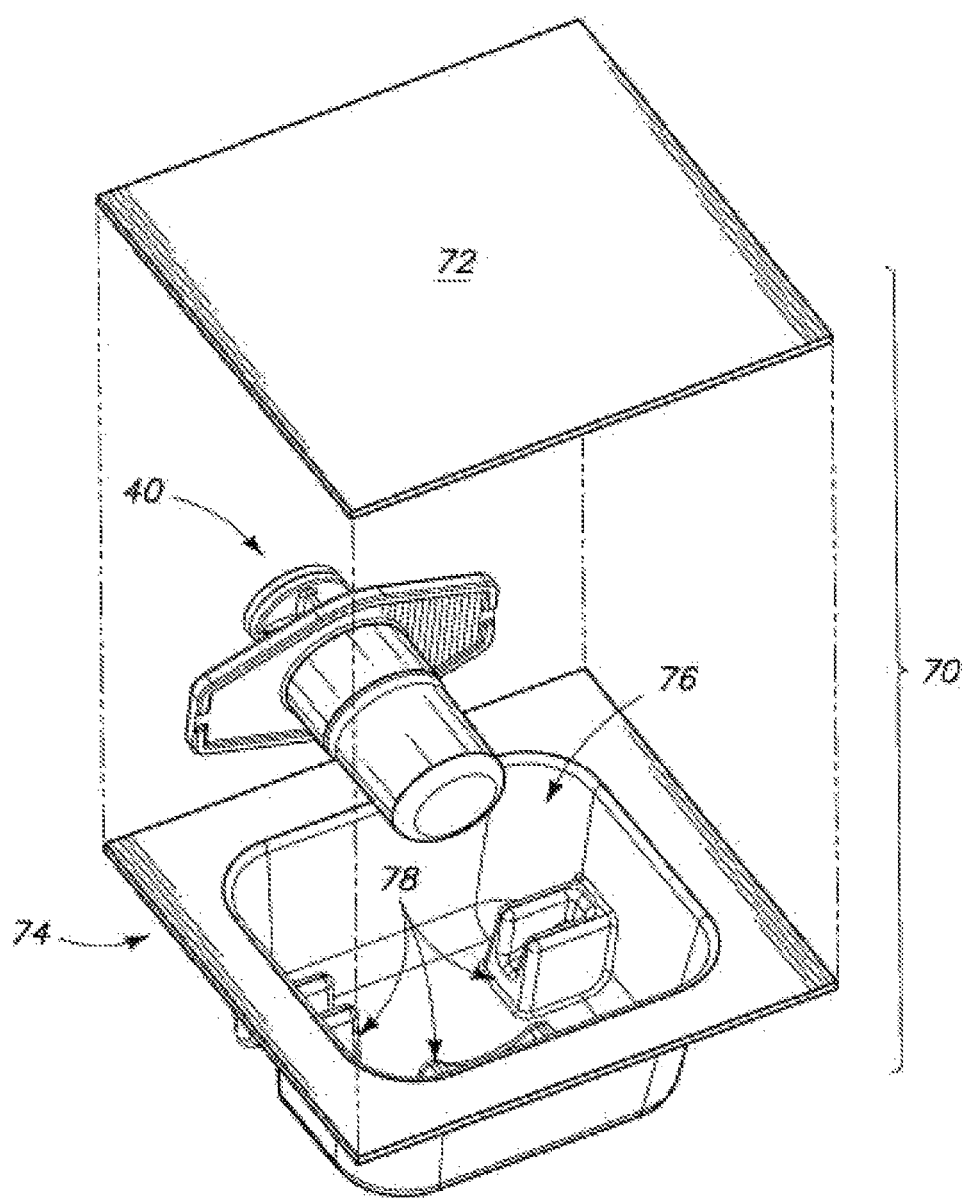
FIG. 10 is a diagrammatic view of an illustrative packaging concept for the device shown in FIG. 6.
Figure 11:
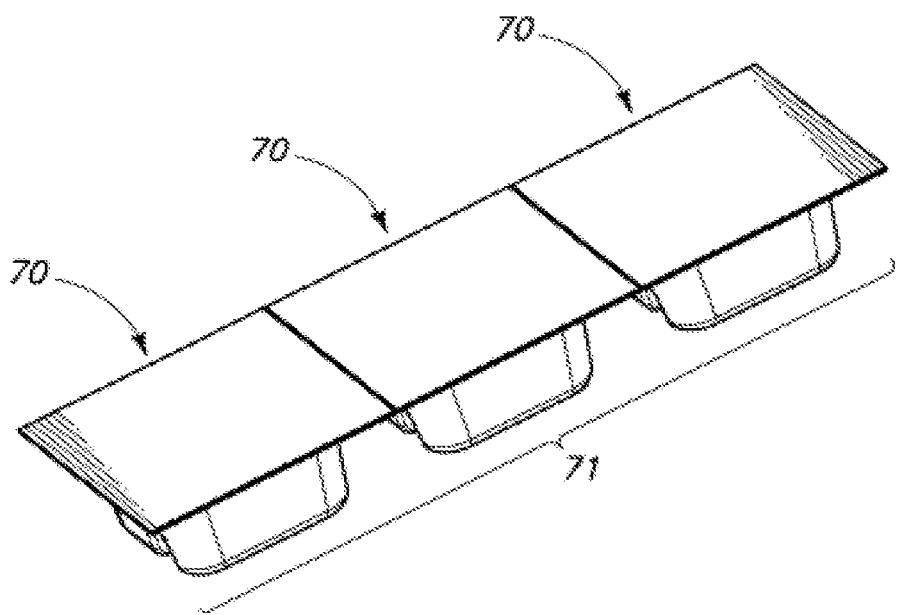
FIG. 11 shows a multi-pack packaging concept for the device shown in FIG. 6.

Referring to FIG. 10 packaging 70 for delivery, storage and/or disposal of the component for access device 40 is illustrated. Such packaging includes a lid 72 and a tray portion 74. Tray portion 74 has a cavity 76 with molded retainers 78 for positioning/retaining of the device and assisting in maintaining the integrity of the device and proper positioning of the plunger relative to the device chamber. Such packaging can be sealed and can be utilized to provide a sterile environment for device 40. As shown in FIG. 11 a series 71 of individual packaging unit 70 can be provided with individually sealed units to allow individual removal of units while maintaining sterility of additional units in the series.

Figure 12:
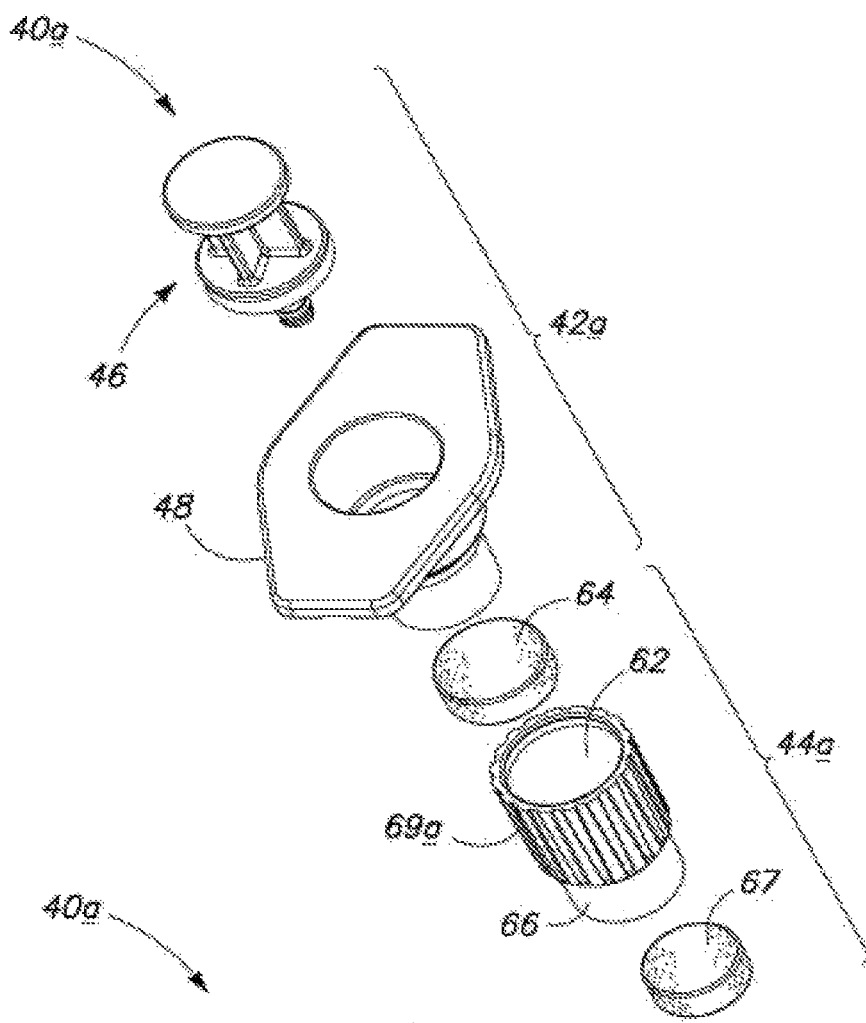
FIG. 12 is a diagrammatic exploded view of a device in accordance with another aspect of the invention.

Another alternative embodiment is described with reference to FIGS. 12-13. In this embodiment first component 42a is the same as the immediately preceding embodiment. However, referring to FIG. 12 second component 44a comprises a "dual cap" system. Cap housing 60a includes container portion 62 and a second cap extension 65 which houses a second container 66. Container 62 can contain an applicator material 64 such as the sponge-like materials described above. Similarly, container 66 can also contain a sponge or other applicator material 67. Container 62 can further contain a cleansing agent such as those described above.

Container 66 can contain one or more microbiocidal agents that differ in composition from the cleaning solution contained in the cleansing cap 62. An example agent composition within cap portion 65 can include from about 3% to about 11% hydrogen peroxide. Additional components of the agent can include for example ethanol (from about 30% to about 40%) sodium citrate (from about 1% to about 4%), EDTA, and/or peracetic acid (less than or equal to about 11%). The pH may be between 5 and 10 and can be adjusted with NaOH or other appropriate base/acid to about ph 7.4 as needed based upon the physiological pH and biocidal activity. The presence of EDTA can provide sporocidal activity against for example bacillus spores by complexing manganese (Mn) and can additionally help stabilize hydrogen peroxide. in combination with hydrogen peroxide in the solution a synergistic and/or additive effect can be achieved. The invention does contemplate use of alternative chelators and pH stabilizers besides those indicated.

It is to be noted that in some instances a similar solution having lower hydrogen peroxide content may be included within the first container 62 and in particular instances may be present within the chamber of the first component.

Figure 13:
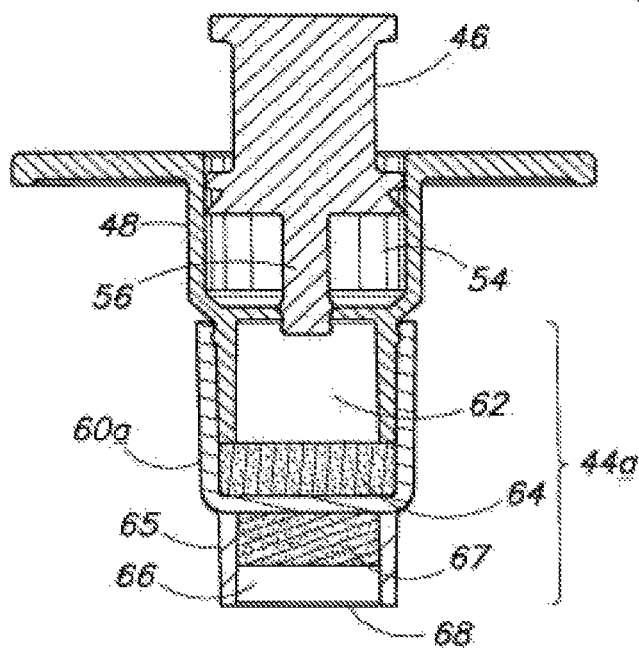
FIG. 13 is a diagrammatic cross-sectional view of the device shown in FIG. 12.

Referring to FIG. 13 such shows an intact device prior to use. In port cleansing applications second component 44a is removed from the device and portion 60a is utilized to cover a port thereby contacting the port with the contents of container 62. Applicator material 64 can assist in applying the cleaning agent to external port surfaces. When the contents of chamber 54 are to be administered, component 44a is removed from the port and first component is attached to the port. Plunger 46 is depressed thereby injecting the contents of chamber 54 into the port. The syringe component is then removed from the port. A removable seal 68 can then be removed from second cap portion 65. Cap portion 65 can be placed over the port such that the contents of container 66 contact the port. Second component 44 can then be removed from the port or can be retained on the port until further port access or manipulation is desired.

Figure 14:
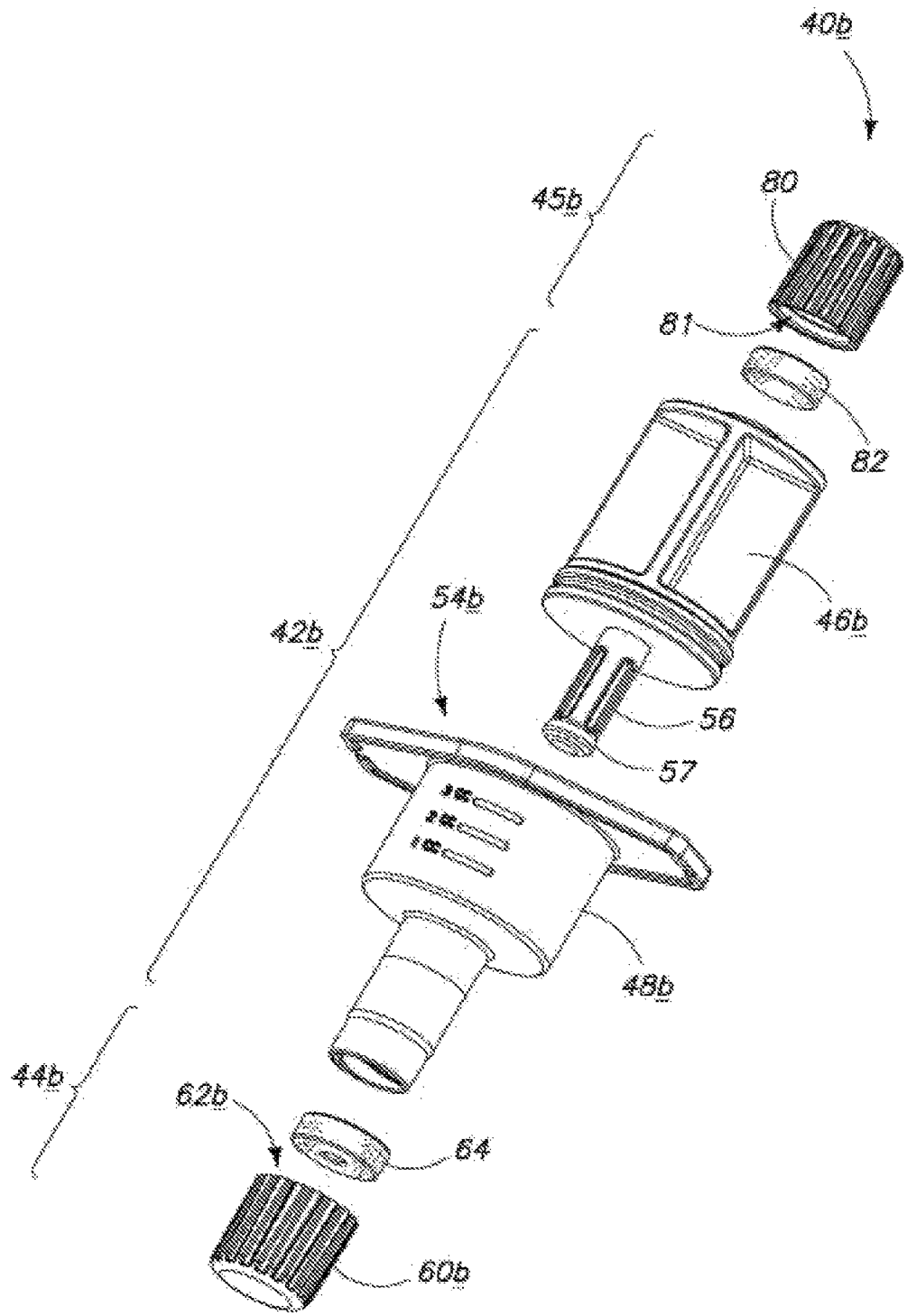
FIG. 14 is a diagrammatic exploded view of a device in accordance with another aspect of the invention.

Referring to FIG. 14 such shows an alternative embodiment wherein port access device 40b comprises a first component 42b, a second component 44b and a third component 45b where second component 44b and third component 45b are independently removable caps. As illustrated the caps are disposed initially at opposing ends of the device and are of differing size. However, alternative relative size and positioning of the caps on the device is contemplated. For example, first component 44b and second 45b can be disposed on top-side or bottom-side of wing extensions 51, 53 of chamber housing 48b.

For the example configuration illustrated, the larger cap (first component 44b) can be removed from the device and can be utilized for external port cleaning in a manner analogous to that described above. The second smaller cap (third component 45b) can be removed from the device after administration of the chamber contents and can be subsequently utilized as a port cap to protect the port until subsequent port access is desired as described above. Third component 45b optionally can contain an applicator material 82 and/or cleansing agent or microbiocidal agent as described above.

Alternative two-cap configurations include a device having a larger cap external to a smaller internal cap, the first cap being removable from the second cap where one of the first and second caps is configured for utilization as a port cap.

In the device shown in FIG. 14, cap housing 60b of second component 44b and cap housing 80 of third component 45b can be of differing colors. As such, the caps can be color coded (or otherwise coded) to notify the user or other personnel of the status of the port or intravascular line. For example, a first color such as green can be utilized on all or a portion of cap housing 80 which will be retained on the port after use of the device to signify a properly sterilized port. Cap housing 60b can be a second color (e.g., yellow or red) signifying the cleansing or other procedure being performed has not yet been completed. Accordingly, the caps can be utilized as an added safety measure to help ensure proper use and assist in maintaining sterility and appropriate record keeping. For example, the caps can allow visual monitoring and can be tracked by hospital pharmacy and/or central auditing software.

In addition to visual auditing of compliance to proper cleaning and maintenance of sterility, a barcode, radio frequency identification (RFID) and/or other pharmacy dispensary or inventory control system associated with the device can be utilized to provide an independent audit/compliance system.

Figure 15:
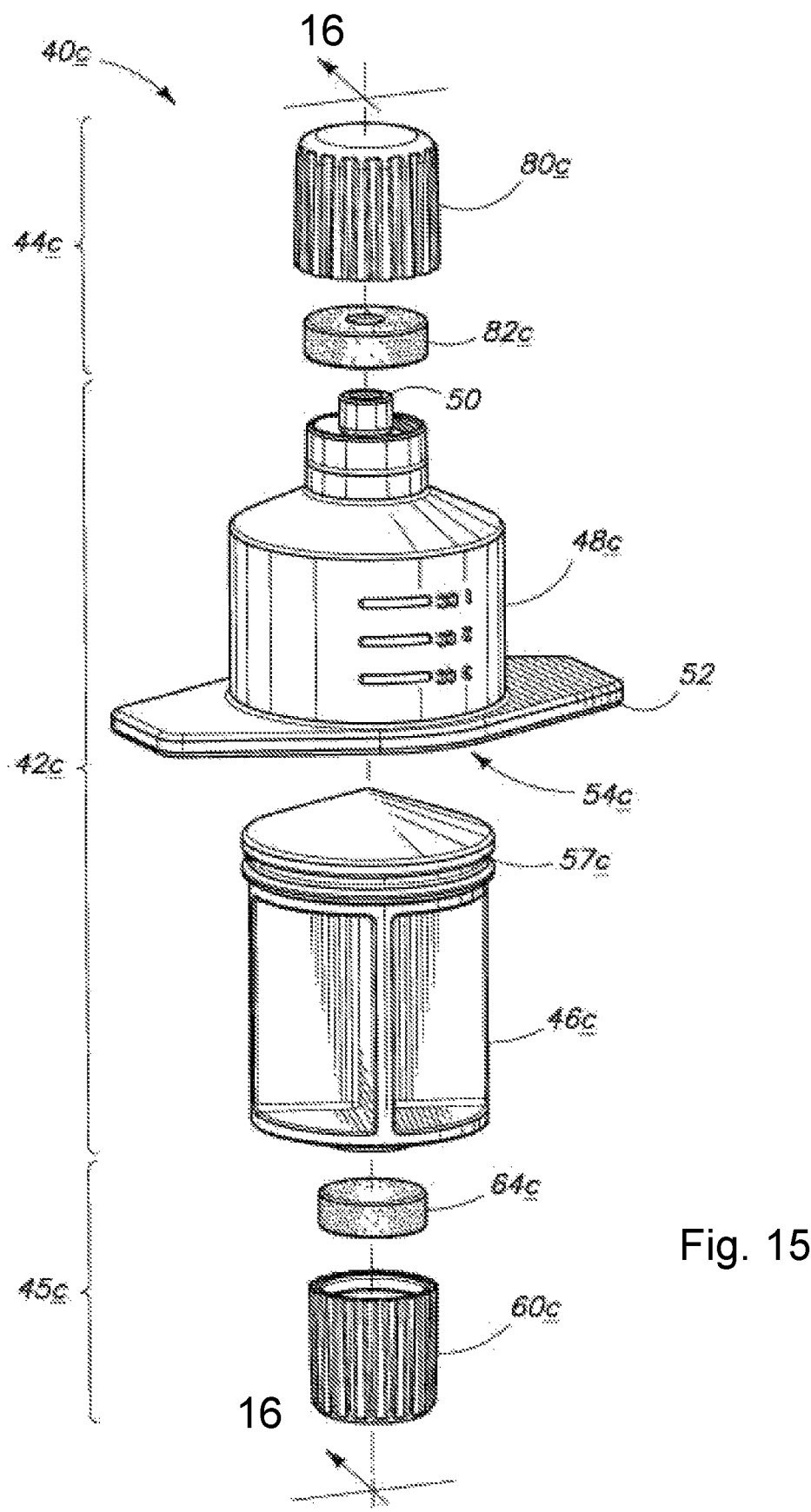
FIG. 15 is a diagrammatic exploded view of a device in accordance with another aspect of the invention.

Referring next to FIG. 15 such depicts an additional alternate embodiment which can utilize a conventional type syringe and plunger design and can utilize caps in accordance with the invention. Accordingly, first component 42c comprises a syringe housing 48c and can have a LEUR-LOK® fitting at first end 50. Plunger 46c can have a conventional type piston seal 57c configured to insert into second end 52 of housing 48c and form a seal with the walls of chamber 54c. Second component 44c can comprise a housing 60c which can for example have an internal receiving port which fits either internally relative to the LEUR-LOK® fitting or which fits over and covers the LEUR-LOK® fitting at first end 50 of first component housing 48c. Third component 45c can also have housing 80c configured such that it comprises an internal receiving port which fits either internally relative to a LEUR-LOK® fitting or which fits over and covers the LEUR-LOK® fitting (or which can have an alternative type fitting) based upon the type of port being cleansed.

Figure 16:
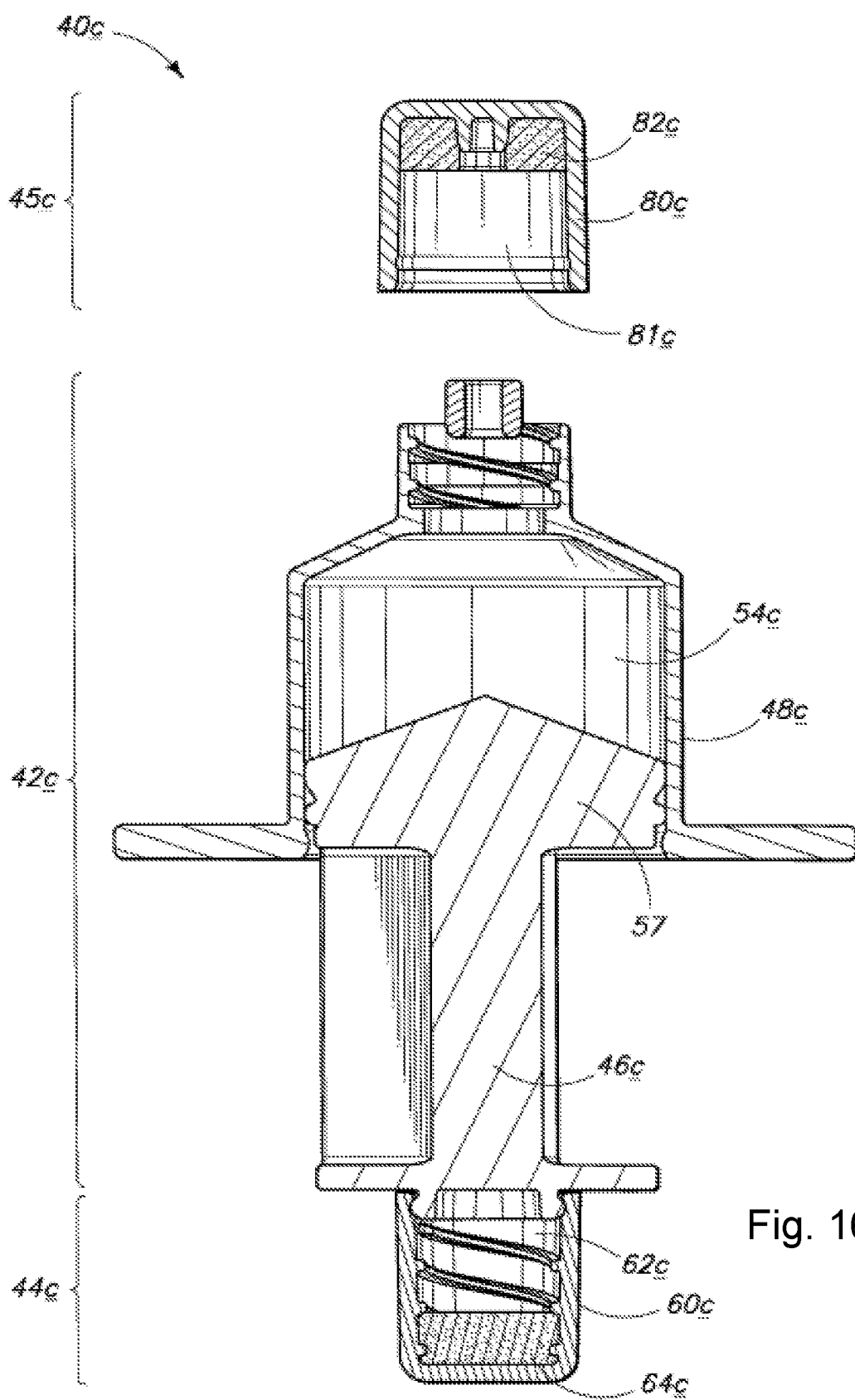
FIG. 16 is a diagrammatic cross-sectional side view of the device shown in FIG. 15.

A cross-sectional view of the device shown in FIG. 15 is illustrated in FIG. 16. Such shows the exemplary type of cap housings for covering LEUR-LOK®-type fittings. For example, third component 45c has housing 80c comprising a portion of such housing which fits internally within a LEUR-LOK® type fitting thereby capping such fitting. In contrast second component 44c has housing 60c which is threaded to thread onto LEUR-LOK® type fitting. It is to be understood that the depiction is for illustrative purposes only and that either or both caps can have the threaded configuration or the snap in configuration. Cap housing 60c and 80c can further be color coded as described above.

The invention also contemplates dual cap system disposed at the distal (non-administration) end of the port cleaner device (not shown). In this dual cap system, a first "green" cap can be reversibly joined to both the device and also back to front in a stack relationship relative to a second "yellow" cap. Each of the two caps can be, for example, a LEUR- LOK® type fitting cap, friction fit cap, etc. The green cap can contain the microbiocide composition described above. The yellow cap can contain for example the cleaning compositions discussed earlier or the microbiocide composition as contained in the green cap since in this configuration the yellow cap is not in contact with the administration end of the device.

Possible materials for caps include, but are not limited to, polyethylene, polypropylene, and/or copolymer materials. Further, the caps can comprise a material or agent that is UV protective to preserve the integrity of hydrogen peroxide during storage, shipping, etc. Packaging may also contain UV protective materials to inhibit hydrogen peroxide breakdown.

As mentioned above, devices of the invention can be utilized for withdrawing blood from an individual through an intravascular catheter or intravascular port. In particular applications, the device can be utilized directly for blood testing purposes. The device chamber can have a chamber size in the range of 1 to 3 ml, with appropriate calibration marks as discussed above. Where whole blood is desired, depending upon the particular purpose for drawing, blood can be drawn into either a device having an empty chamber or into a device containing an anticoagulant such as EDTA, sodium citrate or alternative coagulant (such as discussed above). The device containing blood and anticoagulant can then be utilized directly in blood testing equipment or blood can be transferred to an alternative device for testing.

In applications where serum is desired, whole blood can be drawn into the device chamber and, after coagulation, the device containing the blood sample can be spun to separate the serum from the red blood cells. If anticoagulant is present in the device chamber, further separation can occur to isolate plasma. Alternatively, a filter such as a MIL-LIPORE® (Millipore Corp., Bedford Mass.) filter can be fitted onto the device after a sample is drawn into the device chamber. Such technique can filter out red blood cells, white blood cells and platelets allowing serum to flow from the chamber while retaining the blood cells within the filter. Anticoagulants can optionally be provided within the chamber to allow transfer of blood cells or plasma if such is desired based upon the testing or other procedure to be performed (i.e., complete blood count, CBC, platelet count, reticulocyte count, T and B lymphocyte assays and chemistries).

An appropriate filter can also be utilized to filter out particulates during drawing of a blood sample from an individual into the chamber.

It is to be understood that any of the devices above can be utilized for cleansing purposes, for administration purposes or for blood drawing/testing purposes. Methodology will be analogous with variation based upon the particular device utilized as described above.

Figure 17:
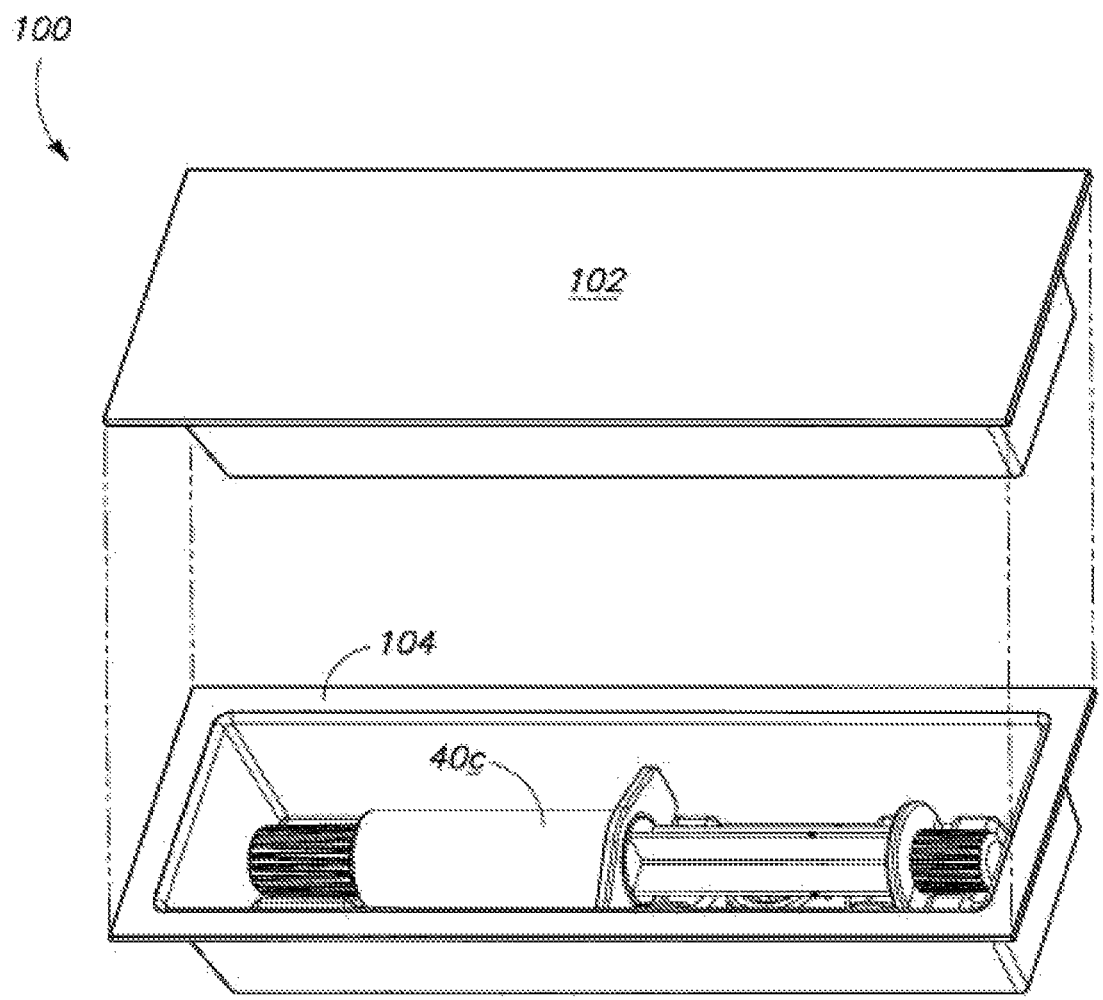
FIG. 17 is a diagrammatic isometric view of a packaging concept in accordance with one aspect of the invention.
Figure 18:
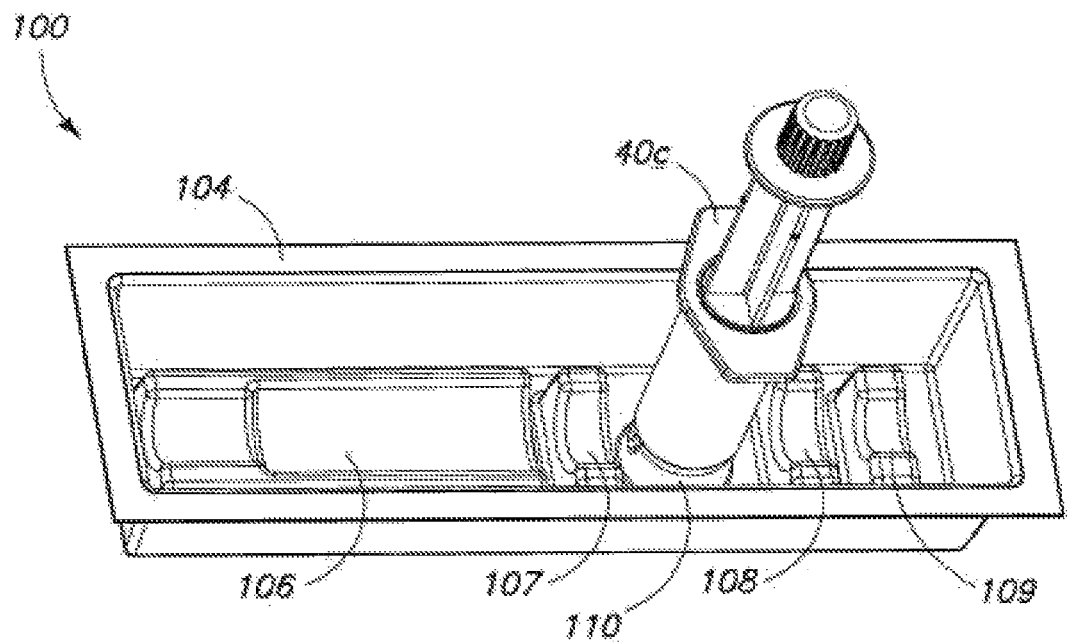
FIG. 18 is a diagrammatic isometric view of the packaging concept shown in FIG. 17.
Figure 19:
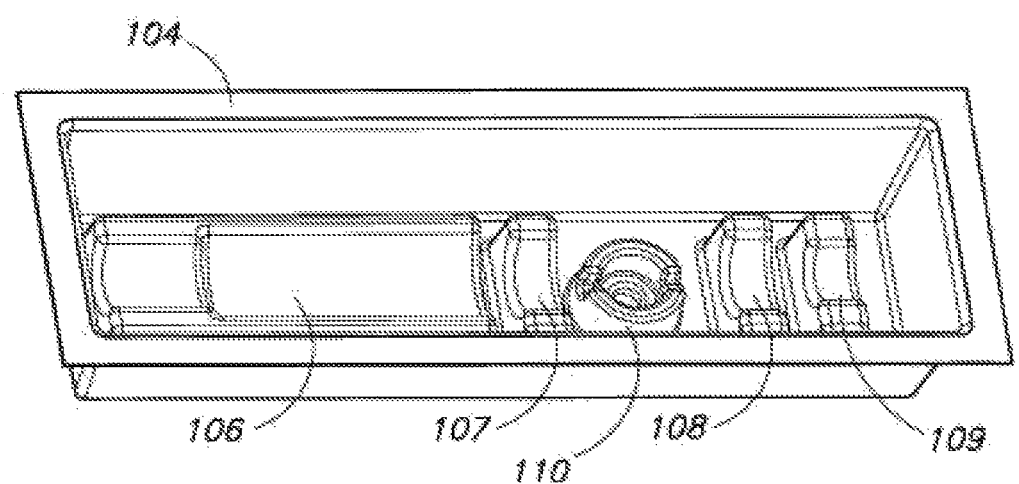
FIG. 19 is another diagrammatic isometric view of the packaging concept shown in FIG. 17.

Example device packaging is illustrated in FIGS. 17-19. Packaging 100 can include a lid portion 102 and a packaging tray 104 as shown in FIG. 17. Referring to FIGS. 18 and 19 packaging tray 104 can be a molded tray which has integrally molded retaining features which conform to the shape of a device 40c in accordance with the invention. The molded features may conform to the shape of the device in the non-deployed position for shipment, storage, etc. Accordingly, tray 104 can have one or more integrally molded retainer features 106, 107, 108, and 109. Tray 104 can also comprise an integrally molded receiving stand 110 which can be configured to receive device 40c in an upright position as depicted in FIG. 18. Such receiving stand can allow device 40c to be inserted and retained during administrative procedures or after use. Tray 104 may also be used for device disposal purposes.

Figure 20:
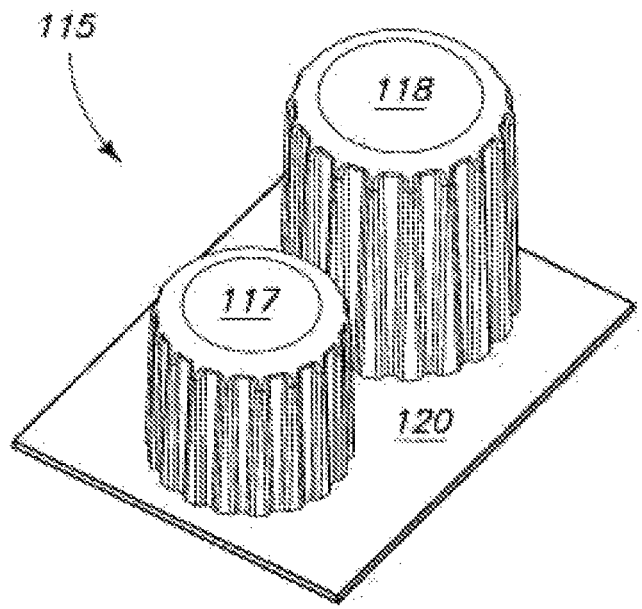
FIG. 20 is a diagrammatic isometric view of a set of components in accordance with one aspect of the invention.
Figure 21:
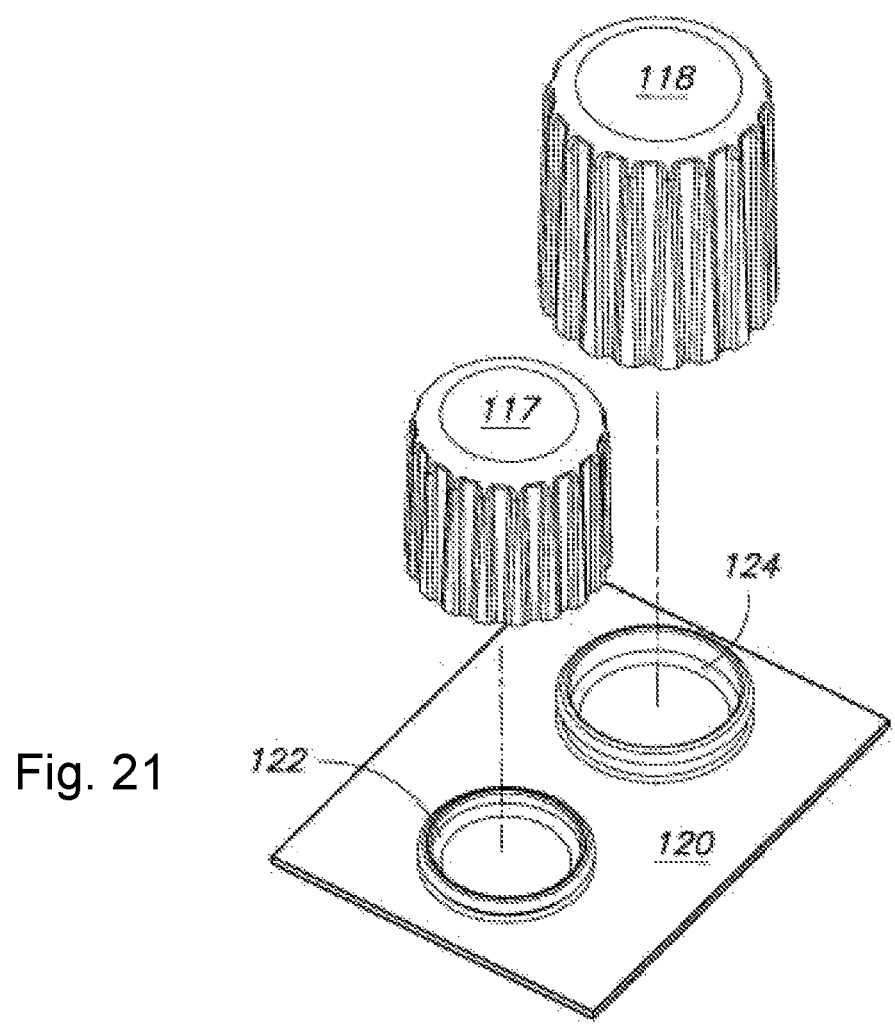
FIG. 21 is an exploded view of the set of components depicted in FIG. 20.

Device caps in accordance with the invention can be utilized independent of the devices for cleansing and protection of alternative access catheters and ports such as intravascular, peritoneal dialysis, urinary ports and catheters, etc. Accordingly, the caps can be packaged independently in pairs (one each of two differing sizes, colors, etc., in groups or in bulk, of one or more colors). FIGS. 20-21 show an example two cap packaging system 115 having a first cap 117 which can be for example a yellow cap and which can be a LEUR-LOK® type cap and a second cap 118 which can be, for example, a green cap and which can also be a LEUR-LOK®. Packaging system 115 can comprise a packaging tray 120 and as illustrated in FIG. 21 can include integrally molded appropriate receiving ports/receiving rings 122, 124. Where additional or fewer caps are to be packaged together tray 120 can have an appropriate number of receiving ports for receiving and reversibly retaining the caps. Where the caps differ in (diametric) size, the ports can also be of differing size as appropriate. It is to be understood that the caps may be provided in groups such as one green and four yellow caps per package or any other appropriate number depending upon the particular procedure for which they will be utilized with the number and size of package ports corresponding to the number and size of various caps.

Figure 22:
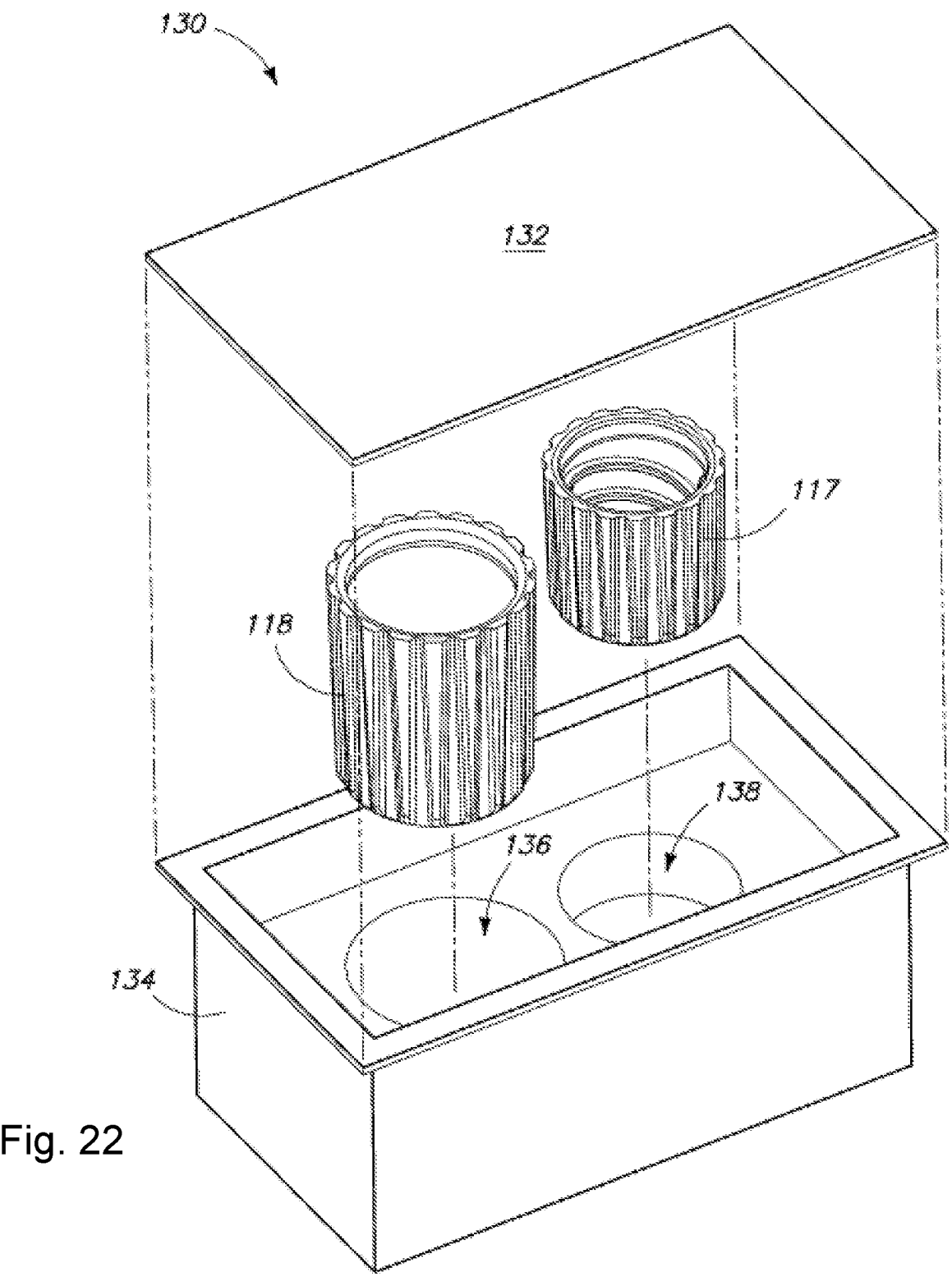
FIG. 22 is a diagrammatic exploded view of a packaging concept in accordance with one aspect of the invention.

Referring next to FIG. 22 an alternative packaging system 130 is illustrated. Packaging system 130 comprises a lid 132 and a tray 130 having integral receiving ports 136 and 138 for receiving caps 117 and 118. As discussed above alternative numbers and sizes of receiving ports can be provided based upon the number and sizes of caps to be utilized.

Where caps are provided in bulk, such may be individually packaged and may be provided individually in sheets or on strips. Caps can alternatively be provided with catheter or line/import devices. Such can be included in common packaging either loose or attached to a port catheter or line to be used for port cleaning and/or protection after package opening and/or while the device is in use. In some instances, the cap(s) can be packaged in one or more sub-packages included within a larger package enclosing the catheter device.

Figure 23:
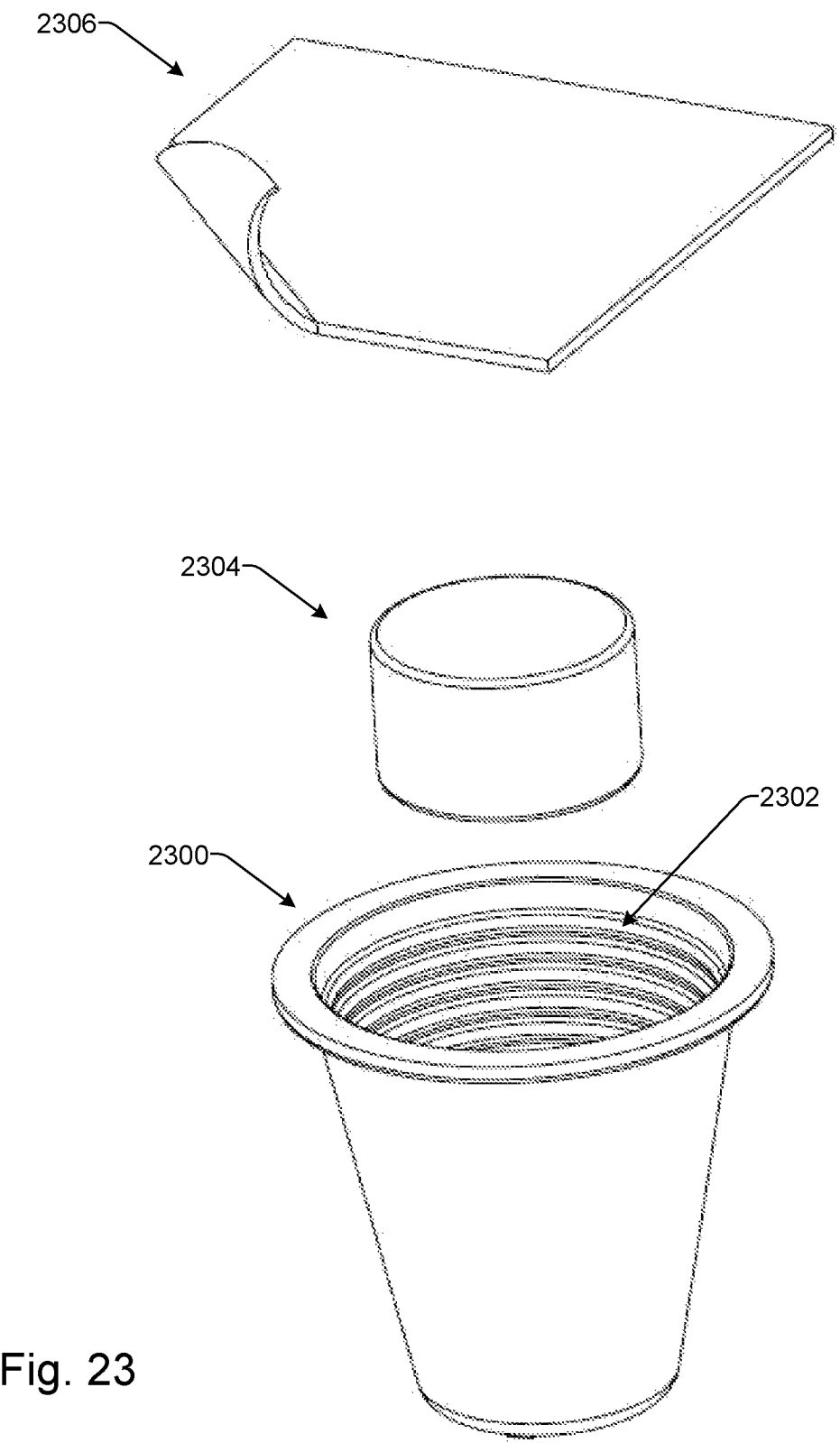
FIG. 23 is a diagrammatic exploded view of a friction fit port cap.

FIG. 23 shows an implementation of a port cap 2300 for covering a port. The port cap 2300 may be implemented as a single use, disposable, sterile cap. The port cap 2300 may have a body that is generally conical in shape with an open end larger than a closed end. In one implementation, the port cap 2300 may have an external shape that is generally cylindrical in which the open end of the port cap 2300 and the closed end of the port 2300 have the same or substantially the same diameter. However, the inside diameter of the port cap 2300 may be larger at the open end and smaller at the closed end. Narrowing of the internal diameter towards the closed end of the port cap 2300 creates an increasingly tight fit as a port is inserted further into the port cap 2300. Wall thicknesses of the port cap 2300 may be between approximately 0.25 mm and 2.5 mm, between approximately 0.5 mm and 2.25 mm, between approximately 0.75 mm and 2 mm, between approximately 1 mm and 1.75 mm, and between approximately 1.25 mm and 1.5 mm. The wall thicknesses of the port cap 2300 may be or approximately 1 mm. Walls of the port cap 2300 may be manufactured with a draft angle of approximately 0° to approximately 30°, from approximately 5° to approximately 25°, from approximately 10° to approximately 20° or approximately 15°. The draft angle of the port cap 2300 may be approximately 12°. The draft angle may assist ejection of the port cap 2300 from a mold during an injection molding process for manufacturing the port cap 2300.

In an implementation, an inside surface of the port cap 2300 includes one or more annular ridges 2302 creating an uneven surface on the inside of the port cap 2300. An annular ridge 2302 may be formed from a portion of material, of either the cap material itself or added material, that extends inward from what would otherwise be a smooth surface on the inside of the port cap 2300. Annular ridges 2302 may also be formed by removing material to create a space or void that extends into the inner wall of the port cap 2300. The presence of annular ridges 2302 through any method of creating results in a structure that has relatively elevated and relatively recessed portions on the inside wall of the port cap 2300. Spaces between the annular ridges 2302 cause portions of the wall of the port cap 2300 to be thinner than the wall of the port cap 2300 would be absent these spaces or "grooves" between the annular ridges 2302. This may provide the port cap 2300 with increased flexibility and ability to stretch over the external surface of a port. Additionally, presence of the greater thickness provided by the annular ridges 2302 relative to the base thickness of the wall of the port cap 2300 absent the annular ridges 2302 provides greater strength. Flexibility in the port cap 2300 provided by the annular ridges 2302 and or use of a flexible material allows the port cap 2300 to stretch while engaging an outer surface of the port then contract when the port cap 2300 fully engages thereby creating a fluid-tight seal. One or more of the annular ridges 2302 compressed against the outside surface of the port with the greatest force may act as gaskets preventing entry or exit of liquid from a capped port.

In an implementation one or more of the annular ridges 2302 may be angled similar to a fish scale or the bottom of a cross-country ski thereby creating a gradual slope as a port is inserted into the port cap 2300 and a steeper slope when the port is removed from the port cap 2300. This asymmetry in the annular ridges 2302 reduces the mechanical force necessary to insert a port into the port cap 2300 and increased the mechanical force necessary to remove the port from the port cap 2300.

The port cap 2300 may include any number of annular ridges 2031 such as, for example, more than one, more than two, more than three, more than four, more than five, more than six, more than seven, more than eight, more than nine, more than 10, more than 11, or more than 12. The entire inside surface of the port cap 2300 may be covered with annular ridges 2302. Alternatively, the annular ridges 2302 may be present on only a portion of the inside of the port cap 2300. The annular ridges 2302 may be arranged as a series of concentric circles of decreasing diameter. The annular ridges 2302 may be uniformly spaced inside the port cap 2300. Alternatively, some or all of the annular ridges 2302 may have an irregular spacing relative to each other.

The external surface of the port cap 2300 is illustrated as a smooth surface. However, in some implementations the external surface may be textured and/or include ribs as shown in caps 117, 118 of FIG. 20.

Possible materials for the port cap 2300 include, but are not limited to, thermoplastic polymers and/or copolymer materials. Example thermoplastic polymers include polyethylene (also called polythene, or poly(methylene)), polypropylene, polylactic acid (polylactide), and polyvinyl chloride (PVC). In an implementation, the port cap 2300 may include an elastomeric material such as, but not limited to, an elastomeric polymer or elastomeric copolymer material. Ethylene-propylene rubbers such as ethylene-propylene-diene (EPDM) are one type of elastomeric polymer. The copolymer material may be ethylene-propylene copolymers (EPM). The material used for the port cap 2300 may be selected to increase gripping strength of the port cap 2300 on an external surface of a port. Additionally, the material used for the port cap 2300 may be selected to provide an outer surface that provides sufficient friction when contacted by human fingers to manipulate the port cap 2300 with reduced slipping.

The port cap 2300 may include an insert of sponge-like material 2304. Illustrative sponge-like materials can include but are not limited to cellulose, polyethylene felt sponge, polyethylene foam sponge, plastic foam sponge, and silicon foam sponge. The sponge-like material may be compressible and formed into various shapes and sizes. One or more separate inserts 2304 may be included inside the port cap 2300. In an implementation the insert 2304 may be larger than the space within the port cap 2300 into which it is inserted and compression of the insert 2304 may hold the insert 2304 inside the port cap 2300. In an implementation the insert 2304 may be adhered to the inside of the port cap 2300 by an adhesive. The insert 2304 may contain a cleansing agent and/or a microbiocidal agent including any of the agents described above.

The port cap 2300 may be colored for ease of identification and to assist healthcare practitioners in confirming that appropriate procedures have been followed for cleaning and covering ports. For example, the port cap 2300 may be purple. Additionally, particular coloration and dyes may be used in the material forming the outer surface of the port cap 2300 as a shield to particular wavelengths of light (e.g., ultraviolet) that could affect the integrity of the port cap 2300 and/or stability of an agent present in the insert 2304.

In order to maintain sterility and prevent loss of liquid present in the insert 2304, the port cap 2300 may include a lid 2306. The lid 2306 may be formed from foil, mylar, polyethylene, polypropylene, copolymer materials, or a laminate formed from multiple layers of different materials (e.g., foil and copolymer). The material of the lid 2306 may be the same or different from the material used to form the port cap 2300.

Figure 24:
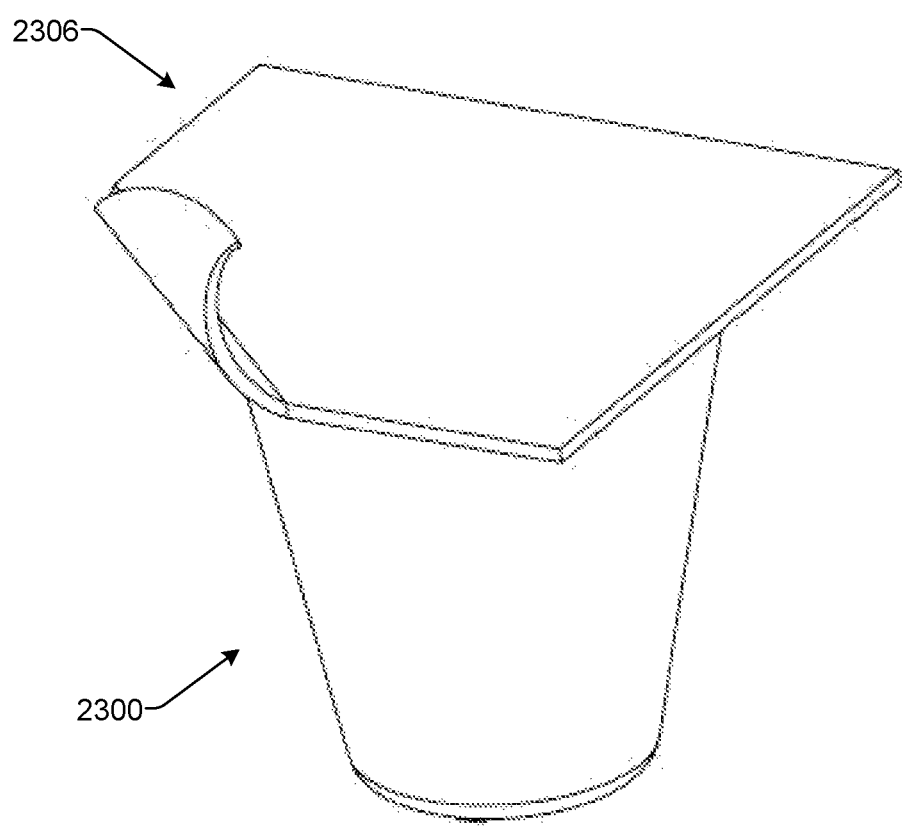
FIG. 24 is a diagrammatic view of the friction fit port cap of FIG. 23 with a lid.

FIG. 24 shows a view of the port cap 2300 covered by the lid 2306. The lid 2306 may be attached to the port cap 2300 during manufacturing (or possibly at a later time) by glue, plastic welding, hot gas welding, use of a thermoplastic welding rod, heat sealing, freehand welding, speed tip welding, extrusion welding, contact welding, hot plate welding, high-frequency welding, induction welding, injection welding, ultrasonic welding, friction welding, spin welding, laser welding, solvent welding, or other technique for creating an attachment that is resistant to separation during shipping, handling, and storage, yet able to be peeled away by hand. The port cap 2300 may be manufactured in a sterile environment so that inside of the inside of the cap once covered by the lid 2306 remains sterile.

Figure 25:
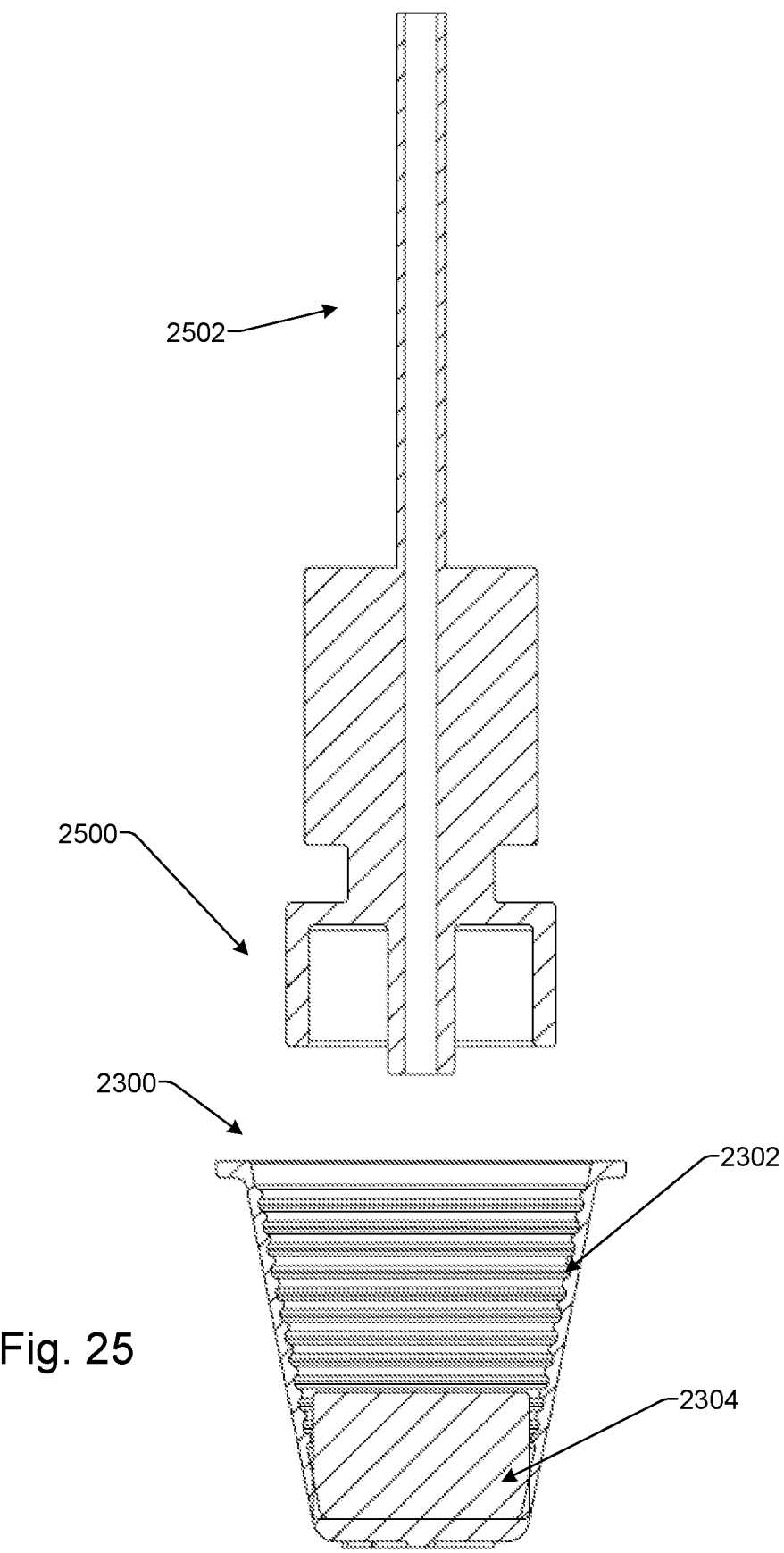
FIG. 25 is diagrammatic cross-sectional view of a friction fit port cap and a LUER-LOK® port.
Figure 26:
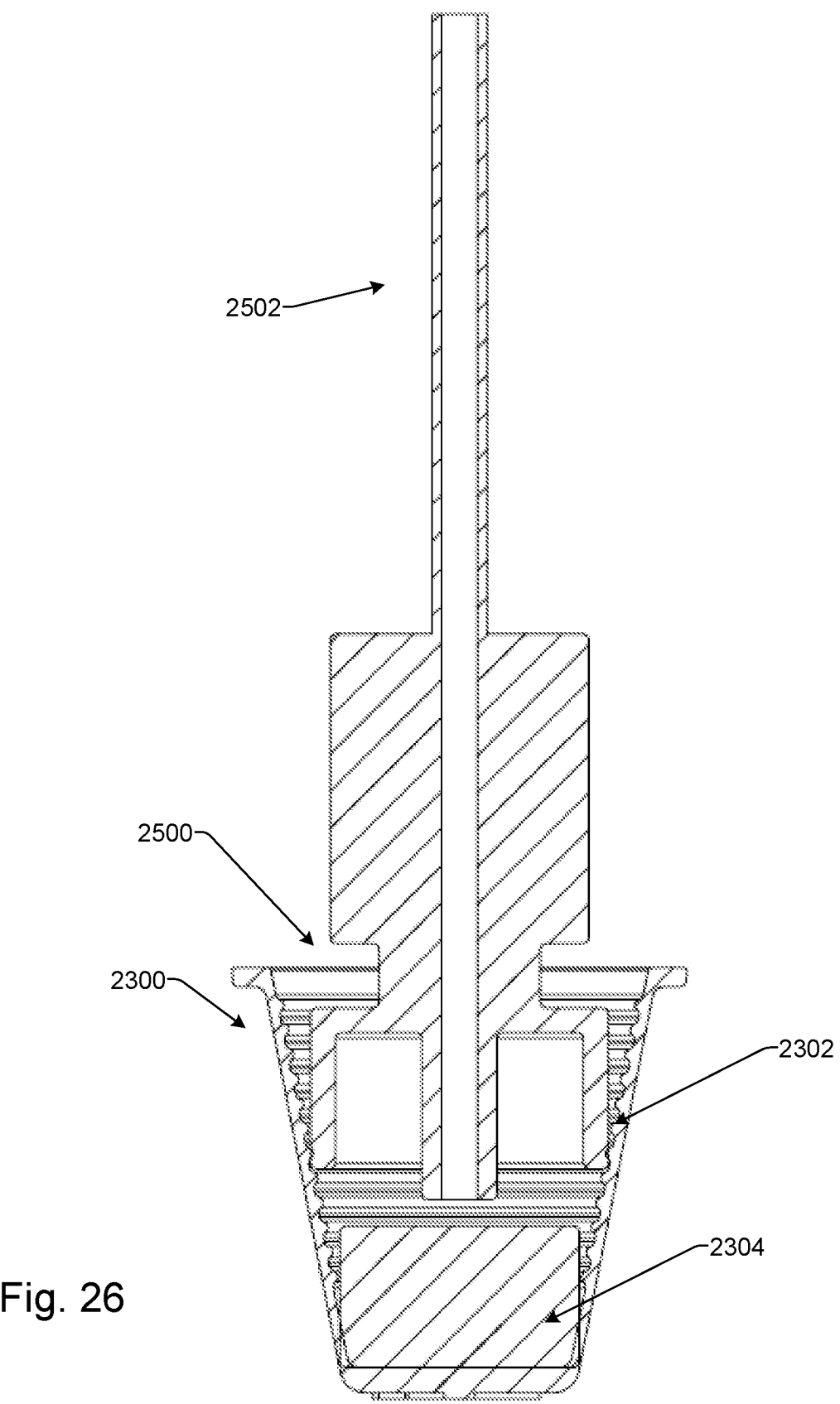
FIG. 26 is a diagrammatic cross-sectional view of the friction fit port cap and the LUER-LOK® port of FIG. 25 with the friction fit port cap engaged on the end of the LUER-LOK® port.
Figure 27:
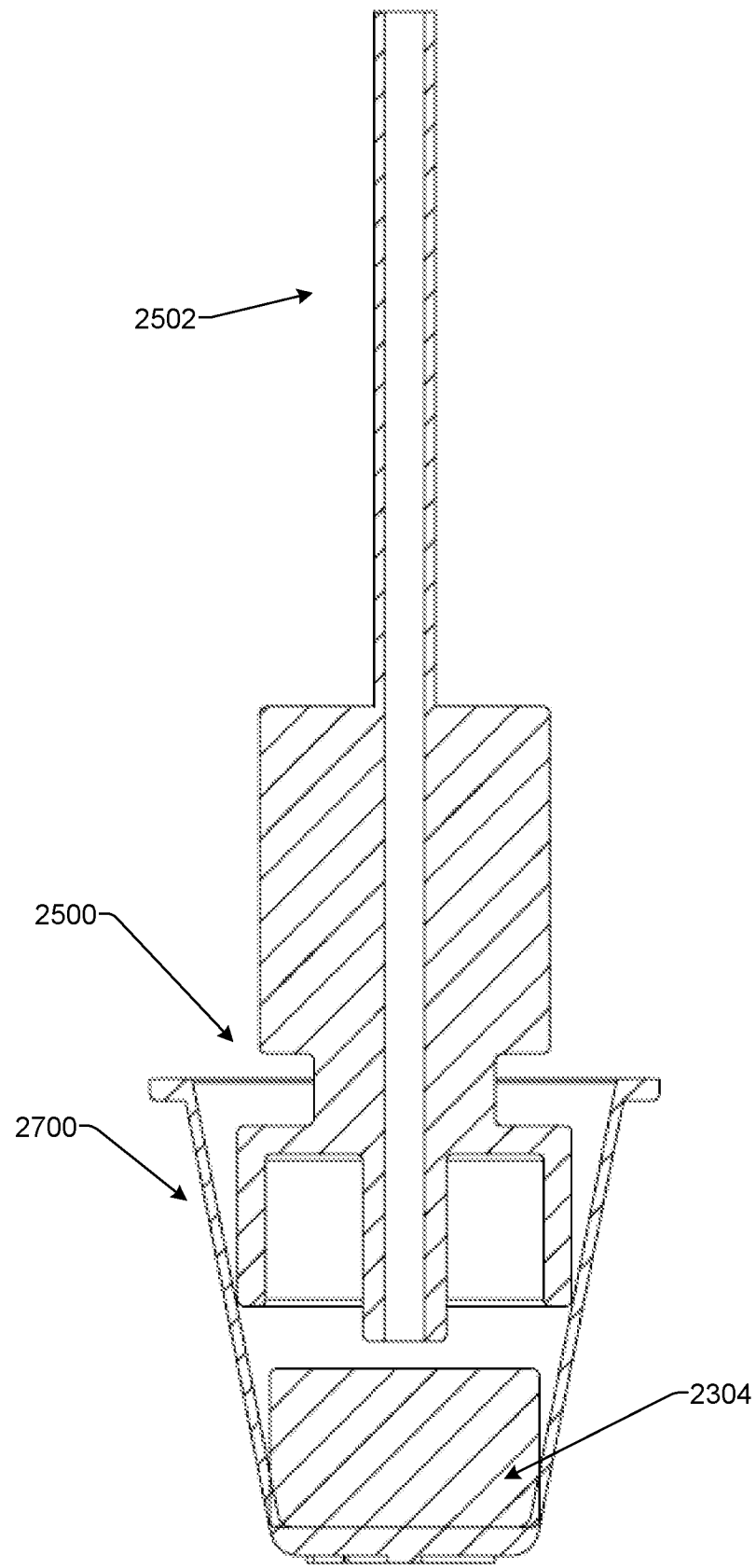
FIG. 27 is a diagrammatic cross-sectional view of an alternative friction fit port cap and a LUER-LOK® port with the friction fit port cap engaged on the end of the LUER-LOK® port.

FIG. 25 shows the port cap 2300 adjacent to an example port, such as a LUER-LOK® port 2500, connected to a piece of tubing 2502. LUER-LOK® ports have internal threads for connecting to catheters, needles, tubing, and other medical equipment. However, the external surface of a LUER-LOK® port 2500 may be generally smooth. In an implementation not shown, the outer surface of the LUER-LOK® port 2500 (or other port type) may also include a raised lip or flange surrounding the proximal end of the port near the opening. Thus, the port cap 2300 fits on the outside and covers the LUER-LOK® port 2500 due to a frictional engagement between the proximal surface edge of the port 2500 and the annular ridges 2302 of the port cap 2300, thereby holding the port cap 2300 in place. Covering the entire opening of the port 2500, as well as at least a part of the outside surface of the LUER-LOK® port 2500 provides a larger barrier and greater protection against contamination than a cover that utilizes the internal threads on the LUER-LOK® port 2500. Although FIGS. 25-27 show the port cap 2300 covering a LUER-LOK® port applications of the port cap 2300 are not so limited and the port cap 2300 may be used to cover other types of ports with different alternative fittings besides a LUER-LOK® fitting. Engagement of the port cap 2300 with the port 2500 may be achieved by direct longitudinal force pushing the port cap 2300 straight onto the port 2500.

FIG. 26 shows the port cap 2300 engaged to cover the LUER-LOK® port 2500. The LUER-LOK® port 2500 is inserted into the port cap 2300 until the internal diameter of the port cap 2300 prevents further insertion. The annular ridges 2302 create friction between the LUER-LOK® port 2500 and the port cap 2300, thereby creating a more secure attachment. The port cap 2300 may be disengaged from the port 2500 by angling the port cap 2300 away from the longitudinal axis of the port 2500 then withdrawing the port cap 2300 from the port 2500. Depending on the relative diameter of the LUER-LOK® port 2500 and the port cap 2300, the end of the LUER-LOK® port 2500 may or may not be in direct contact with the insert 2304. The agent present in the insert 2304 may sterilize or otherwise clean the end of the LUER-LOK® port 2500. If the end of the LUER-LOK® port 3500 does not directly contact the insert 2304 the agent may drain from the insert 2304 during transport, storage, or other times and contact the LUER-LOK® port 2500.

FIG. 27 shows an implementation similar to that illustrated in FIG. 26 with a port cap 2700 that has an internal surface without annular ridges 2301. In this implementation, friction is also used to hold the port cap 2700 over the LUER-LOK® port 2500 (or other type of port). In one implementation the inside surface of the port cap 2700 may be textured by creating the port cap 2700 out of a material that has a textured surface. The inner surface of a port cap 2700 that is manufactured from a smooth material such as hard plastic may be textured by abrasion, exposure to chemical solvents, or other techniques. Similarly, external surfaces of the port cap 2700 may be textured to increased ability of users to grip the port cap 2700 with fingers.

CLAUSES

Clause 1. A port cap for an intravascular port, the port cap comprising:
a closed end;
an open end having a larger diameter than a diameter of the closed end; and
a conical body including a flexible material, an inside of the conical body having a plurality of annular ridges,
the port cap configured to be stretched over the intravascular port so that one or more of the plurality of annular ridges forms a fluid-tight seal over an opening of the intravascular port.

Clause 2. The port cap of clause 1, wherein the flexible material comprises a thermoplastic polymer, an elastomeric material, or both.

Clause 3. The port cap of clause 1 or 2, wherein the annular ridges are uniformly spaced on the inside of the conical body.

Clause 4. The port cap of clause 1, 2, or 3, wherein the annular ridges are asymmetrical having a slope facing the open end that is less than a slope facing the closed end.

Clause 5. The port cap of clause 1, 2, 3, or 4, wherein an outer surface of the port cap is colored with a dye that shields the port cap from ultraviolet light.

Clause 6. The port cap of clause 1, 2, 3, 4, or 5, wherein a wall thickness of the conical body is from 0.25 mm to 2.5 mm.

Clause 7. The port cap of clause 1, 2, 3, 4, 5, or 6, wherein a draft angle of the conical body is from 0° to 30°.

Clause 8. The port cap of clause 1, 2, 3, 4, 5, 6, or 7, wherein a wall thickness of the conical body is 1.0 mm and a draft angle of the conical body is 12°.

Clause 9. The port cap of clause 1, 2, 3, 4, 5, 6, 7, or 8, wherein the port cap includes an insert.

Clause 10. The port cap of clause 9, wherein the insert contains a cleaning agent, a microbiocidal agent, or both.

Clause 11. The port cap of clause 9 or 10, wherein the insert comprises cellulose, polyethylene felt sponge, polyethylene foam sponge, plastic foam sponge, silicon foam sponge, or a combination thereof.

Clause 12. The port cap of clause 1, 2, 3, 4, 5, 6, 7, 8, 9, 10, or 11, further comprising a lid attached to the open end and configured to maintain sterility inside the port cap.

Clause 13. A method of engaging the port cap of clause 1, 2, 3, 4, 5, 6, 7, 8, 9, 10, 11, or 12 with a port to form a fluid-tight seal by applying direct longitudinal force to push a portion of the port cap over an external surface of the port.

Clause 14. A method of disengaging the port cap of clause 1, 2, 3, 4, 5, 6, 7, 8, 9, 10, 11, or 12 from a port comprising:
applying force to angle the port cap away from a longitudinal axis of the port; and
withdrawing the port cap away from the port.

Clause 15. The method of clause 13 or 14, wherein the port comprises a port having internal threads.

The invention has been described in language more or less specific as to structural and methodical features. It is to be understood, however, that the invention is not limited to the specific features shown and described, since the features disclosed herein comprise illustrative forms of putting the invention into effect. The invention is, therefore, claimed in any of its forms or modifications within the proper scope of the appended claims.

The invention claimed is:

1. A port cap for an intravascular port, the port cap comprising:
a closed end;
an open end having a larger diameter than a diameter of the closed end; and
a conical body including a flexible material, an inside of the conical body having a plurality of annular ridges, the annular ridges being asymmetrical, whether engaged with a port or not, and having a slope facing the open end that is less than a slope facing the closed end,
the port cap configured to be stretched over the intravascular port so that one or more of the plurality of annular ridges forms a fluid-tight seal over an opening of the intravascular port.

2. The port cap of claim 1, wherein the flexible material comprises a thermoplastic polymer, an elastomeric material, or both.

3. The port cap of claim 1, wherein the annular ridges are uniformly spaced on the inside of the conical body.

4. The port cap of claim 1, wherein an outer surface of the port cap is colored with a dye that shields the port cap from ultraviolet light.

5. The port cap of claim 1, wherein a wall thickness of the conical body is from 0.25 mm to 2.5 mm.

6. The port cap of claim 1, wherein a draft angle of the conical body is from 0° to 30°.

7. The port cap of claim 1, wherein a wall thickness of the conical body is 1.0 mm and a draft angle of the conical body is 12°.

8. The port cap of claim 1, wherein the port cap includes an insert.

9. The port cap of claim 8, wherein the insert contains a cleaning agent, a microbiocidal agent, or both.

10. The port cap of claim 8, wherein the insert comprises cellulose, polyethylene felt sponge, polyethylene foam sponge, plastic foam sponge, silicon foam sponge, or a combination thereof.

11. The port cap of claim 1, further comprising a lid attached to the open end and configured to maintain sterility inside the port cap.

12. A method of engaging the port cap of claim 1 with a port to form a fluid-tight seal by applying direct longitudinal force to push a portion of the port cap over an external surface of the port.

13. A method of disengaging the port cap of claim 1 from a port comprising:
  applying force to angle the port cap away from a longitudinal axis of the port; and
  withdrawing the port cap away from the port.

14. The method of claim 12, wherein the port comprises a port having internal threads.

15. The method of claim 13, wherein the port comprises a port having internal threads.

* * * * *